US010478552B2

(12) United States Patent
Cronenberg et al.

(10) Patent No.: US 10,478,552 B2
(45) Date of Patent: *Nov. 19, 2019

(54) DRUG DELIVERY DEVICE

(71) Applicant: Becton, Dickinson and Company, Franklin Lakes, NJ (US)

(72) Inventors: Richard A. Cronenberg, Mahwah, NJ (US); Lionel Vedrine, Palo Alto, CA (US); Paul Alchas, Franklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 258 days.

This patent is subject to a terminal disclaimer.

(21) Appl. No.: 15/208,330

(22) Filed: Jul. 12, 2016

(65) Prior Publication Data

US 2017/0049958 A1 Feb. 23, 2017

Related U.S. Application Data

(63) Continuation of application No. 13/698,894, filed as application No. PCT/US2011/030182 on Mar. 28, 2011, now Pat. No. 9,408,985.

(Continued)

(51) Int. Cl.
*A61M 5/142* (2006.01)
*A61M 5/145* (2006.01)
(Continued)

(52) U.S. Cl.
CPC ...... *A61M 5/14248* (2013.01); *A61M 5/1454* (2013.01); *A61M 5/3287* (2013.01);
(Continued)

(58) Field of Classification Search
CPC .............. A61M 5/3287; A61M 5/1454; A61M 5/14248; A61M 2005/14252
See application file for complete search history.

(56) References Cited

U.S. PATENT DOCUMENTS

| 5,858,001 A | 1/1999 | Tsals et al. |
| 5,957,895 A | 9/1999 | Sage et al. |

(Continued)

FOREIGN PATENT DOCUMENTS

| EP | 1 064 035 B1 | 11/2003 |
| EP | 1495775 | 1/2005 |

(Continued)

*Primary Examiner* — Bradley J Osinski
(74) *Attorney, Agent, or Firm* — Dickinson Wright PLLC

(57) ABSTRACT

The subject invention provides a drug delivery device for injecting medicament which includes: a tubular reservoir; a stopper slidably disposed in the reservoir; a spring for moving the stopper in the reservoir; at least one needle, the needle having a distal end for insertion into a patient, and a lumen extending proximally from the distal end, the lumen being in direct or indirect communication with the reservoir; a needle driver for displacing the needle; and, an actuator. Activation of the actuator causes the spring to move the stopper and the needle driver to displace the needle. The needle moves relative to, and separately from, the reservoir with the needle being displaced. Advantageously, with the subject invention, a drug delivery device is provided wherein a needle is moved, relative to the reservoir, in being displaced for injection. This permits control of the needle displacement separate from the reservoir.

11 Claims, 23 Drawing Sheets

US 10,478,552 B2
Page 2

Related U.S. Application Data

(60) Provisional application No. 61/346,542, filed on May 20, 2010.

(51) Int. Cl.
  *A61M 5/32* (2006.01)
  *A61M 5/46* (2006.01)

(52) U.S. Cl.
  CPC ........... *A61M 5/14566* (2013.01); *A61M 5/46* (2013.01); *A61M 2005/1426* (2013.01); *A61M 2005/14252* (2013.01); *A61M 2205/581* (2013.01); *A61M 2205/582* (2013.01)

(56) References Cited

U.S. PATENT DOCUMENTS

| | | |
|---|---|---|
| 6,595,956 B1 | 7/2003 | Gross et al. |
| 6,824,529 B2 | 11/2004 | Gross et al. |
| 6,843,782 B2 | 1/2005 | Gross et al. |
| 7,384,413 B2 | 6/2008 | Gross et al. |
| 7,455,663 B2 | 11/2008 | Bikovsky |
| 9,408,985 B2 * | 8/2016 | Cronenberg ...... A61M 5/14248 |
| 2003/0109827 A1 | 6/2003 | Lavi et al. |
| 2004/0010207 A1 | 1/2004 | Flaherty et al. |
| 2006/0095014 A1 | 5/2006 | Ethelfeld |
| 2006/0135913 A1 | 6/2006 | Ethelfeld |
| 2012/0123387 A1 * | 5/2012 | Gonzalez ........ A61M 37/0015 604/506 |

FOREIGN PATENT DOCUMENTS

| | | |
|---|---|---|
| JP | 11-313889 | 11/1999 |
| JP | 2000-515394 A | 11/2000 |
| JP | 2001-512992 A | 8/2001 |
| JP | 2005-538773 A | 12/2005 |
| JP | 2006-501878 A | 1/2006 |
| JP | 2006-525046 A | 11/2006 |
| JP | 2010-501281 | 1/2010 |
| WO | WO-1997/021457 A1 | 6/1997 |
| WO | WO-03/049789 A1 | 6/2003 |
| WO | WO-2004/006982 A2 | 1/2004 |
| WO | WO-2004/024211 A2 | 3/2004 |
| WO | WO-2004/032990 A2 | 4/2004 |
| WO | WO-2004/089684 A1 | 10/2004 |
| WO | WO-2004/098682 A2 | 11/2004 |
| WO | WO-2004/098684 A2 | 11/2004 |
| WO | WO-2008/024810 A2 | 2/2008 |
| WO | WO-2009062508 A1 | 5/2009 |
| WO | WO-2010003886 A1 | 1/2010 |
| WO | WO-2010/033770 A2 | 3/2010 |
| WO | WO-2011/014514 A1 | 2/2011 |

* cited by examiner

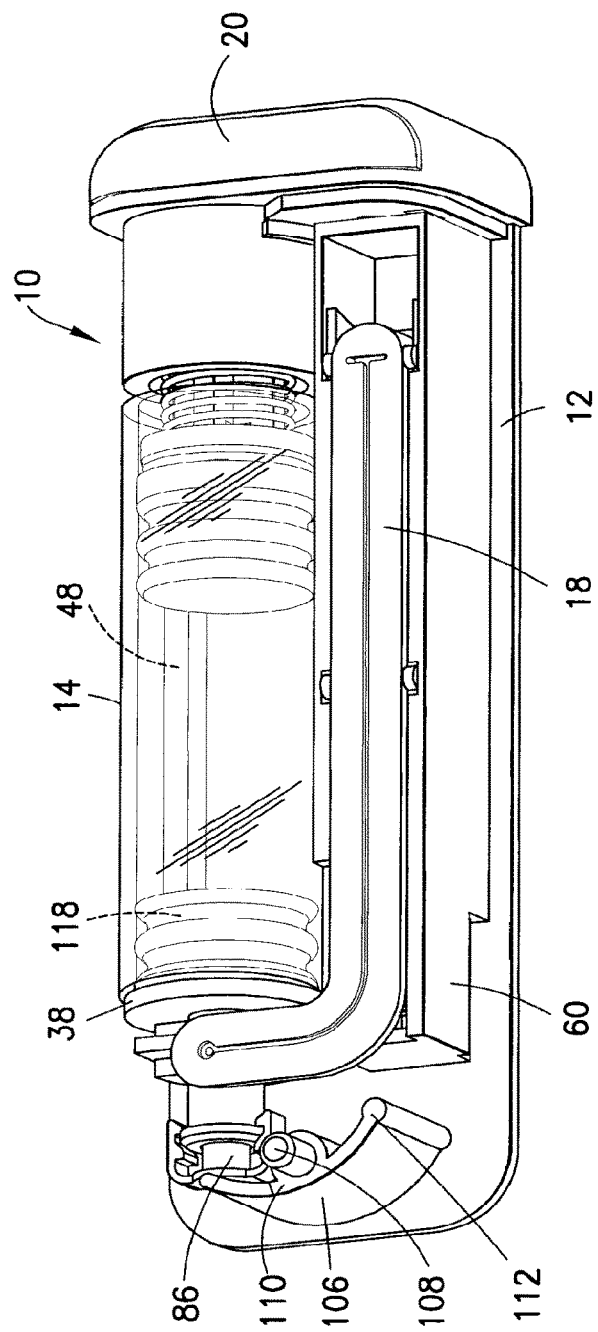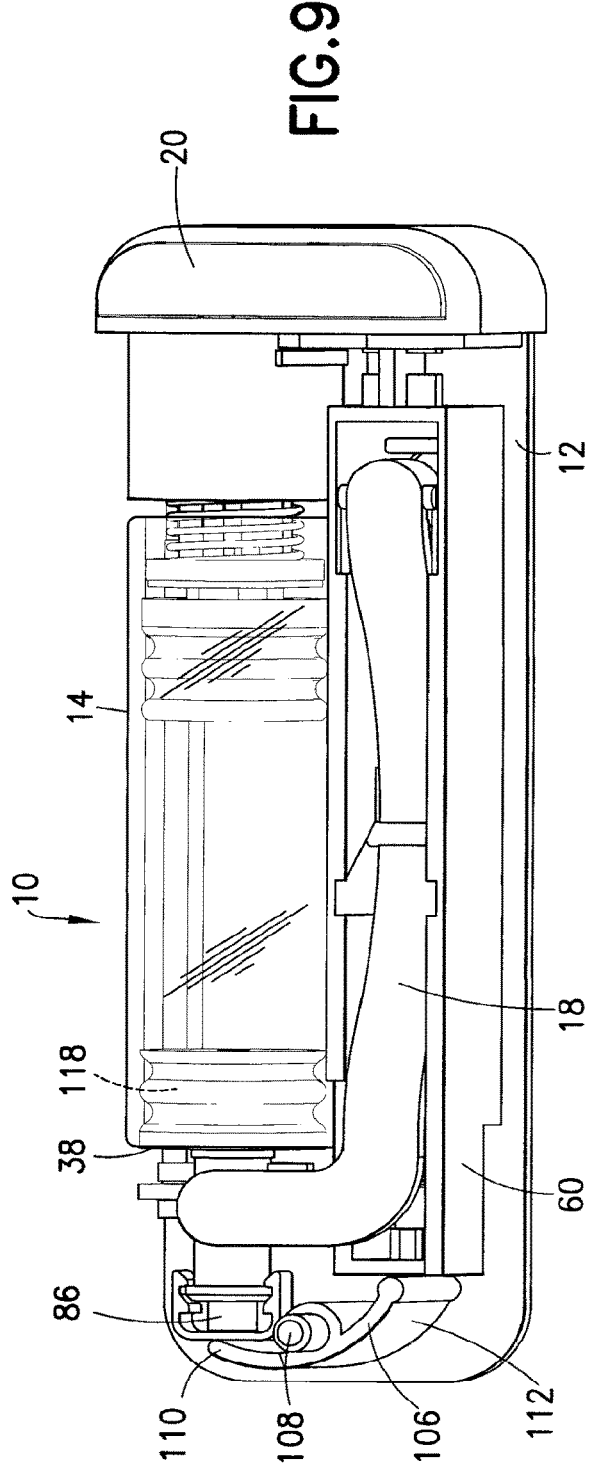

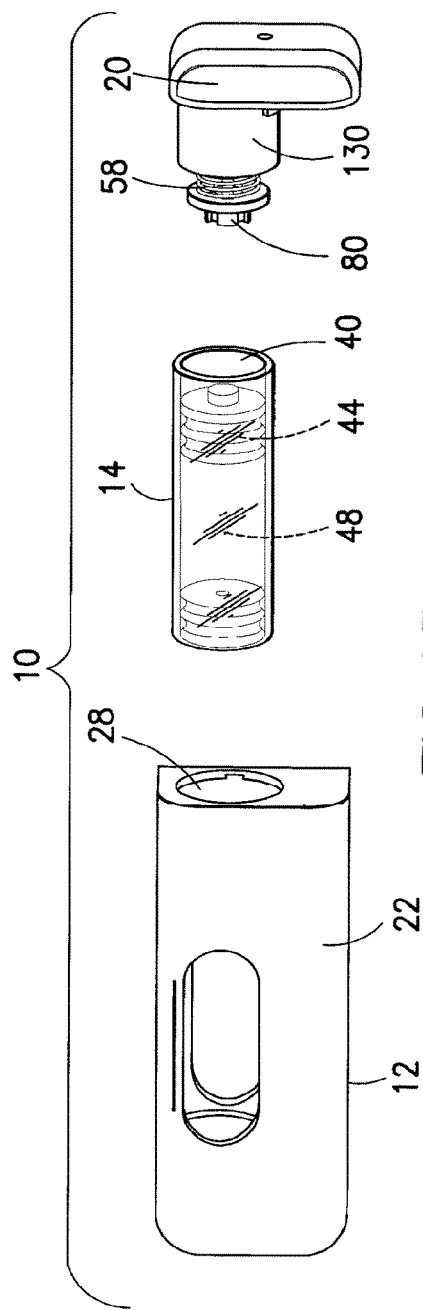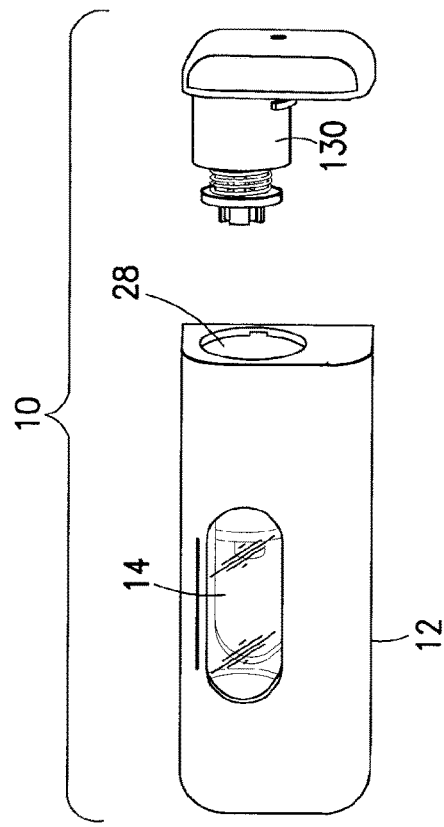
FIG.15
FIG.16

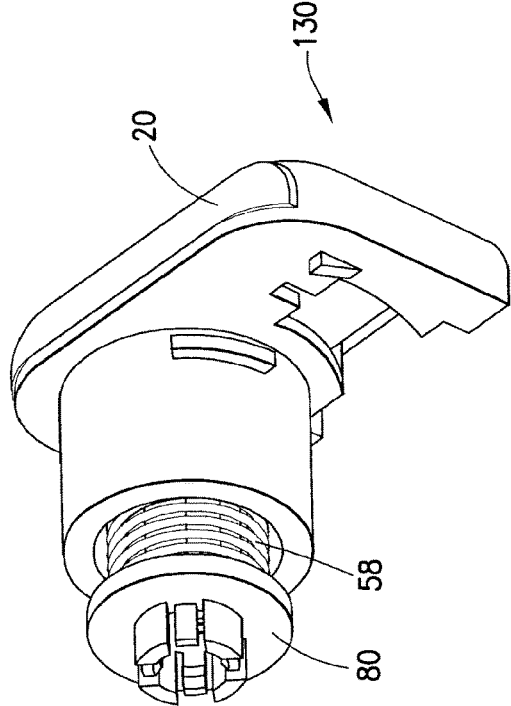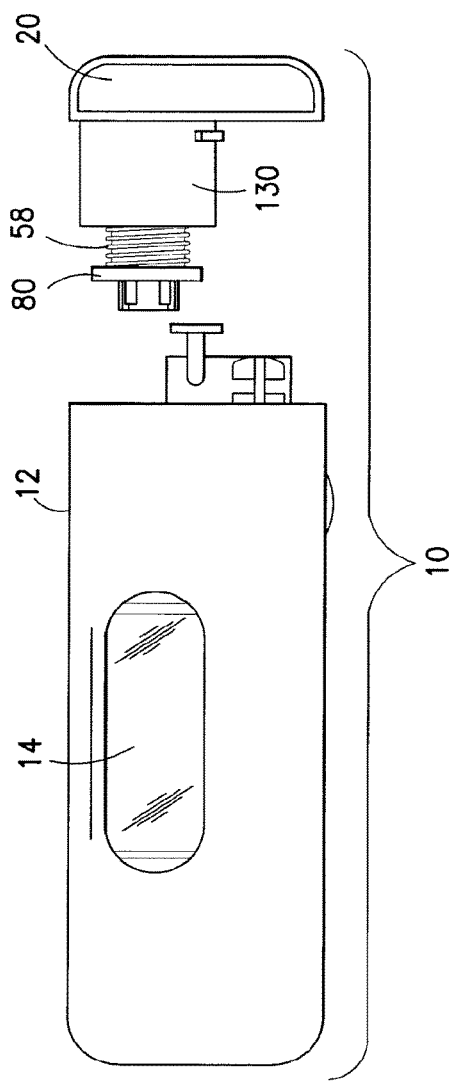

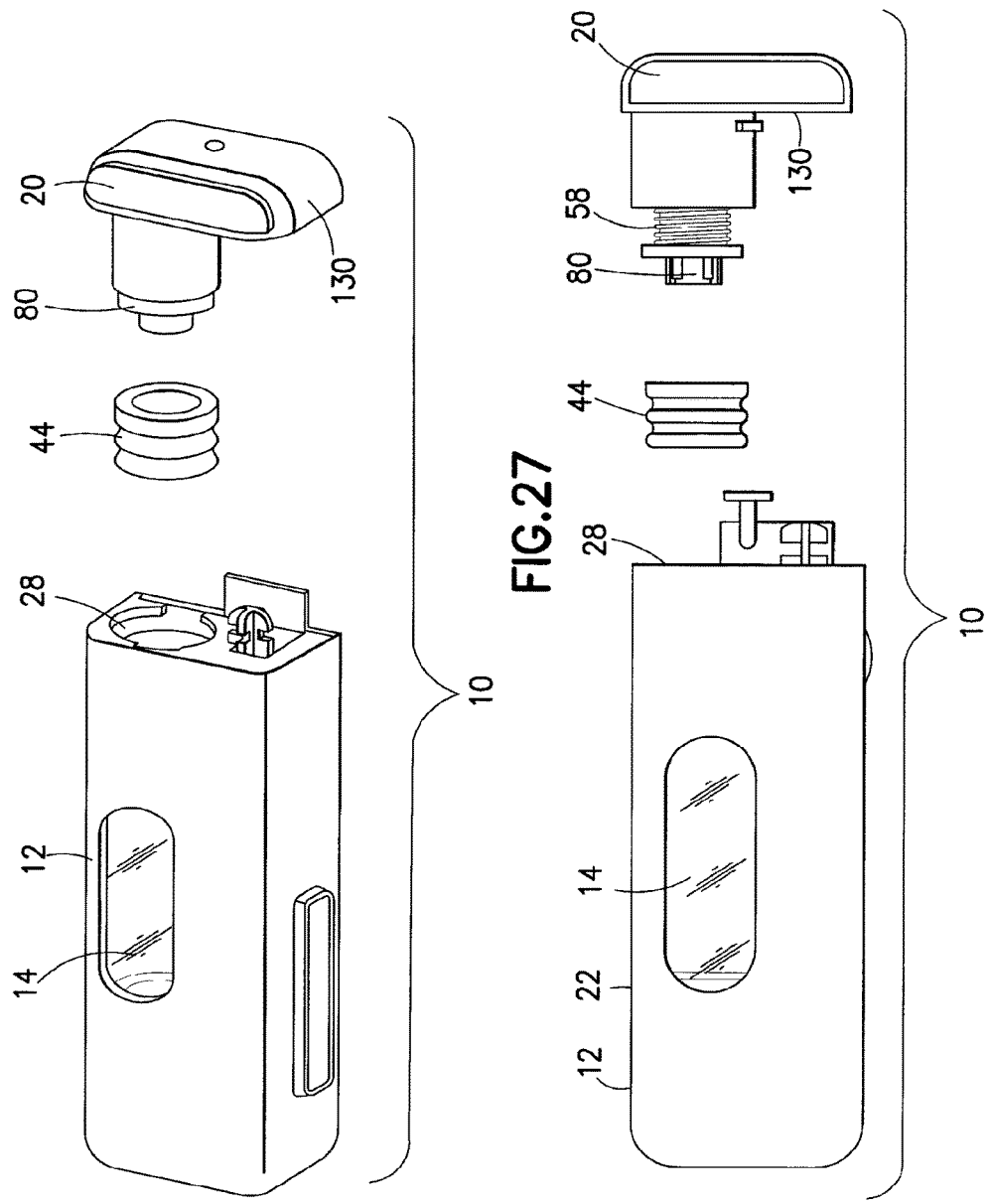

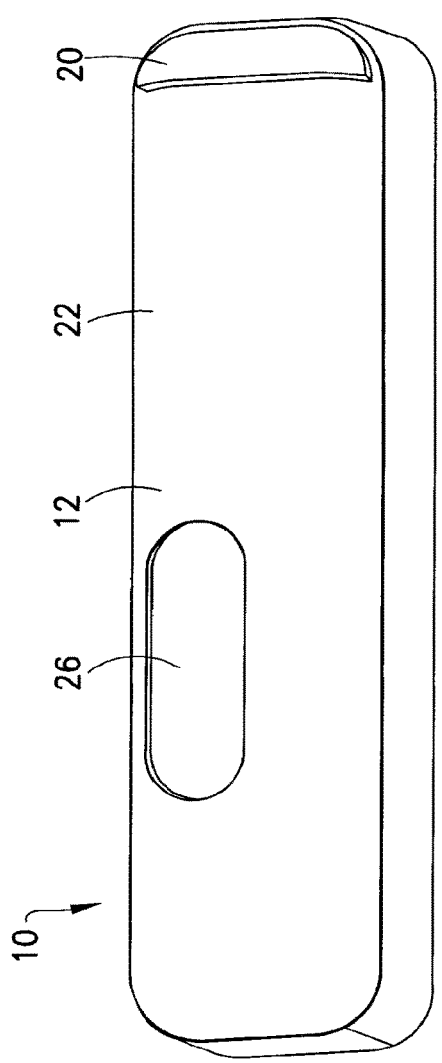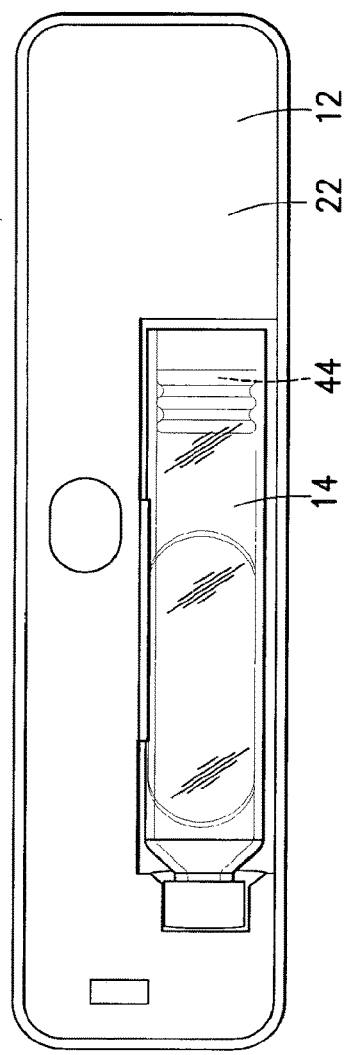

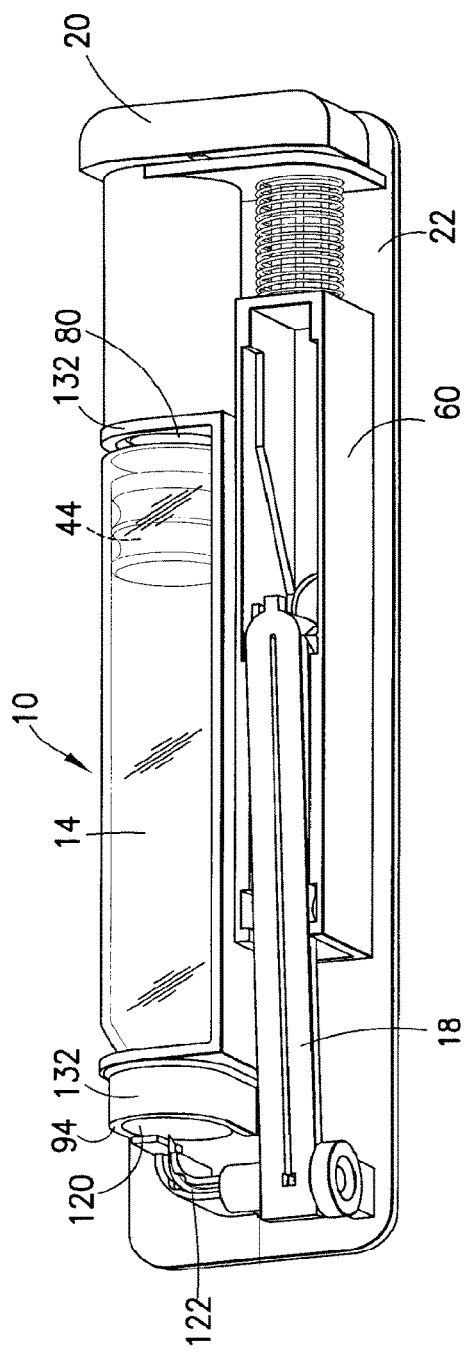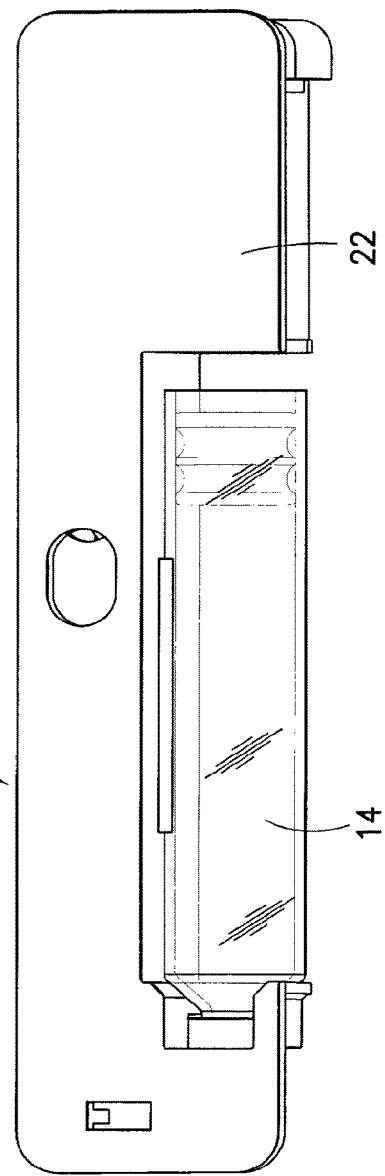

DRUG DELIVERY DEVICE

RELATED APPLICATIONS

This application is a continuation of U.S. patent application Ser. No. 13/698,894, filed on Nov. 19, 2012, which is the U.S. national stage of International Application No. PCT/US11/30182, filed on Mar. 28, 2011, which claims priority to U.S. Provisional Application Ser. No. 61/346,542, filed on May 20, 2010, each of these applications being hereby incorporated by reference in their entirety.

FIELD OF THE INVENTION

This invention relates to drug delivery devices for parenteral administration of medicament.

BACKGROUND OF THE INVENTION

Drug delivery devices in the form of infusers are known in the prior art for administering medicament to a patient. Infusers are intended for mounting onto a patient's skin for self-administration of a medicament. Activation of the infuser not only provides for injection of a needle into a patient's skin, but also to cause auto-drive of a plunger to drive medicament into the patient via the injected needle. Typical infuser constructions have the needle fixed to the reservoir. For example, with reference to U.S. Pat. No. No. 5,858,001 to Tsals et al., an infuser is disclosed which is activated through swivel displacement of a reservoir-containing body. A needle is attached to the Tsals et al. device which is also caused to penetrate the skin of a patient with the swivel displacement of the body. The needle is fixed to the body so as to move therewith. Other types of infusers are known, including those which use standard needle-mounted syringe barrels. With infusers, the ability to independently control the injection of the needle, from the administration of medicament, is limited.

SUMMARY OF THE INVENTION

The subject invention provides a drug delivery device for injecting medicament which includes: a tubular reservoir for accommodating a medicament; a stopper slidably disposed in the reservoir; a spring for moving the stopper from a first position to a second position in the reservoir; at least one needle, the needle having a distal end for insertion into a patient, and a lumen extending proximally from the distal end, the lumen being in direct or indirect communication with the reservoir; a needle driver for displacing the needle from a first state to a second state; and, an actuator. Activation of the actuator causes the spring to move the stopper from the first position and towards the second position, and the needle driver to displace the needle from the first state and towards the second state. The needle moves relative to, and separately from, the reservoir with the needle being displaced from the first state and towards the second state. Advantageously, with the subject invention, a drug delivery device is provided wherein a needle is moved, relative to the reservoir, in being displaced for injection. This permits control of the needle displacement separate from the reservoir.

As used herein, the term "distal", and derivatives thereof, refers to a direction towards a patient during use. The term "proximal", and derivatives thereof, refers to a direction away from a patient during use.

These and other features will be better understood through a study of the following detailed description and accompanying drawings.

BRIEF DESCRIPTION OF THE DRAWINGS

FIGS. 4-14 show different states of a needle driver useable with the subject invention;

FIGS. 15-19 show different configurations of a drug delivery device formed in accordance with the subject invention;

FIGS. 27-28 show a method of loading a drug delivery device formed in accordance with the subject invention;

FIGS. 29-33 show an alternative method of loading a drug delivery device formed in accordance with the subject invention;

DETAILED DESCRIPTION OF THE INVENTION

Figure 1:
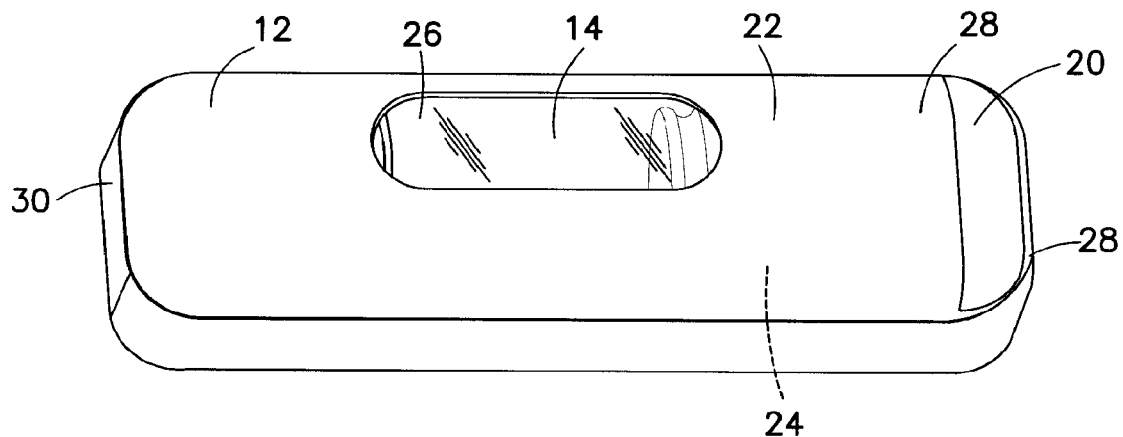
FIG. 1 is a perspective view of a drug delivery device formed in accordance with the subject invention.

With reference to the Figures, a drug delivery device is shown and designated with the reference numeral 10. The drug delivery device 10 generally includes a body 12 accommodating a reservoir 14, at least one needle 16, a needle driver 18, and an actuator 20. The drug delivery device 10 is for injecting drugs or medicament, these terms being used interchangeably herein, into a patient and is particularly well-suited to be mounted onto a patient's skin for self-administration, as discussed below. Any form of medicament, e.g., liquid or slurry, including one or more pharmaceutically-active agents, may be administered by the drug delivery device 10, as will be recognized by those skilled in the art.

The body 12 includes a shell 22 encompassing a closed volume 24. The closed volume 24 is preferably sized and configured to accommodate the working components of the infuser 10 so as to be wholly contained therewithin. The shell 22 is preferably formed of a thermoplastic, but may be formed of other polymeric and/or metallic materials. To ease manufacturing, the shell 22 may be formed of one or more components which snap, or are otherwise assembled, together. One or more openings may be formed in the shell 22 for different purposes. For example, one or more windows 26 may be provided positioned to permit visual observation of the reservoir 14. In addition, one or more access openings 28 may be provided to permit access to a component, such as the actuator 20. The shell 22 may also include one or more removable panels 30, which also permit access to the interior of the shell 22, such as to permit filling of the reservoir 14.

The body 12 may be of various shapes. As shown in the Figures, the body 12 may have a generally rectangular box shape. Other shapes are possible. It is preferred that the body 12 include a generally flat skin mounting surface 32 on which preferably is disposed adhesive 34. The adhesive 34 may be of any type which permits mounting of the infuser 10 to a patient's skin for use and later removal thereof The adhesive 34 may be a low tack pressure sensitive adhesive, but other forms may also be useable. An access opening 28' is formed to extend through the shell 22 at the skin mounting surface 32 and is formed to permit passage therethrough of the needle 16, as described below. Preferably, the adhesive 34 bounds the needle access opening 28'.

The reservoir 14 is preferably a tubular barrel. The reservoir 14 is preferably of a circular cross-section, but may be of other cross-sectional shapes. In addition, it is preferred that the reservoir 14 be formed of glass, but may be also formed of a polymeric material. With a tubular configuration, the reservoir 14 includes a wall 36 extending between first and second ends 38, 40 with a lumen 42 extending therebetween. A stopper 44 is slidably disposed in the reservoir 14 particularly in sealing engagement with the wall 36 within the lumen 42. The stopper 44 is preferably of an elastomeric material and is formed in any manner known in the art.

Figure 4:
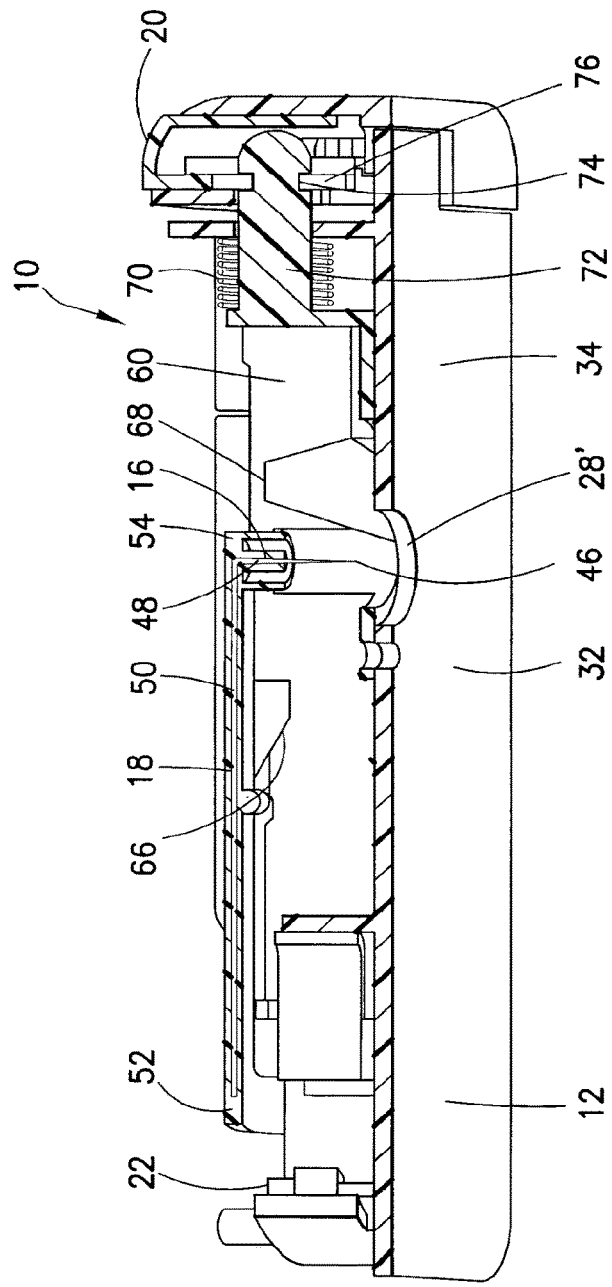
Figure 6:
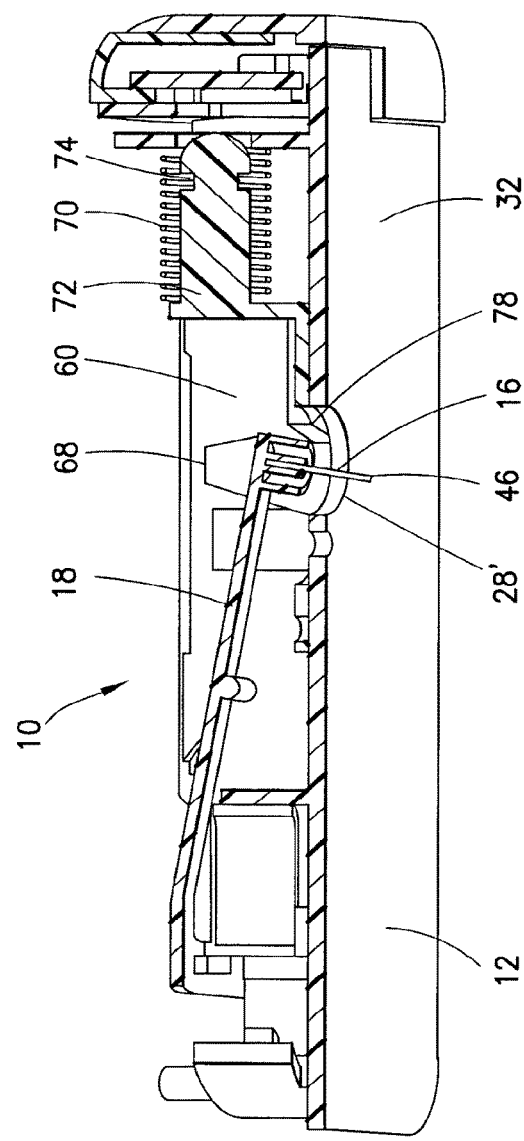

The at least one needle 16 is mounted to the needle driver 18. Reference herein shall be to the use of a single needle, but, as will be recognized by those skilled in the art, a plurality of needles may be likewise utilized. The needle driver 18 is configured to displace the needle 16 from a first state to a second state. The first state may coincide with the needle 14, more particularly a distal end 46 of the needle 14, being contained within the body 12 (FIG. 4). The second state may coincide with the distal end 46 of the needle 16 being exposed externally of the body 12 to be in an injection position (FIG. 6). The needle 16 and the distal end 46 may be formed in any known manner for injecting into a patient.

The needle 16 includes a lumen 48 which extends proximally from the distal end 46. The lumen 48 is in direct or indirect communication with the reservoir 14. With direct communication, an open passage is defined between the reservoir 14 and the lumen 48. More preferably, a breachable seal arrangement or adjustable valve is in the flowpath between the reservoir 14 and the lumen 48 so as to permit selective communication therebetween. With this arrangement, inadvertent flow from the reservoir 14 and through the lumen 48 may be minimized, particularly during transportation and storage.

In a preferred arrangement, a flow channel 50 extends from the lumen 48 and through the needle driver 18 into communication with the reservoir 14. In a preferred arrangement, the needle driver 18 is in the form of a deformable cantilevered arm having a fixed end 52 and a free end 54. The needle 16 is fixed at or near the free end 54 using any known technique. Preferably, the needle driver 18 is formed of thermoplastic, with the needle 16 being formed of a metallic material. The needle 16 may be adhered and/or molded into the needle driver 18. The flow channel 50 is defined to extend through the needle driver 18 into communication with the lumen 48.

The needle driver 18 may be of various configurations which achieve displacement of the needle 16. The needle driver 18 is caused to displace under motive force which may be generated from internal resilience of the needle driver 18 or applied from an external source, such as a spring or other force applicator. With reference to FIG. 4, it is preferred that the needle driver 18 be in a flat, unbiased state prior to use. In this manner, plastic deformation of the needle driver 18 into an undesired state may be avoided. It is possible to have the free end 54 of the needle driver 18 held in a deflected state, where internal resilience of the needle driver 18 may provide spring force for displacing the needle 16. Any form of retaining mechanism may be used to releasably retain the needle driver 18 in the deflected state. However, maintenance of the needle driver 18 in the deflected state may result in plastic deformation thereof with little or no spring back upon release of the retaining mechanism. Although the needle driver 18 may be configured to overcome the situation through material choice, it is preferred that the needle driver 18 be formed generally flat so as to not provide a deflected, or otherwise deformed, state.

The drug delivery device 10 is configured, such that upon activation, medicament is caused to be auto-driven from the reservoir 14 and, separately, the needle 16 is caused to be displaced so as to be inserted into a patient. It is preferred that a single actuation of the actuator 20 be utilized to achieve such dual effect. Various actuator configurations may be utilized. By way of non-limiting example, the actuator 20 may be of a displaceable button-type which is configured for linear displacement. As will be appreciated by those skilled in the art, other actuators may be utilized.

A spring 58 is provided for moving the stopper 44 from a first position to a second position in the reservoir 14. Movement of the stopper 44 causes displacement of the medicament from the reservoir 14. In an initial, pre-use state, a retaining arrangement is provided to retain the stopper 44 in the first position against force of the spring 58. Upon actuation of the actuator 20, the retaining arrangement is released, thus permitting movement of the stopper 44 to the second position. Simultaneously, actuation of the actuator 20 results in the needle driver 18 displacing the needle 16 so as to inject a patient. Medicament, under force of movement of the stopper 44, is caused to flow through the needle 16 so as to be administered to a patient.

The actuation of the needle driver 18 may be achieved in various manners. In a preferred embodiment, an elongated, trough-shaped needle actuator 60 may be provided coextensive with at least a portion of the needle driver 18. One or more detents 62 extend from the needle driver 18 to ride along tracks or other features formed in the needle actuator 60. In a preferred arrangement, the needle actuator 60 is caused to be linearly displaced relative to the needle driver 18 causing the detents 62 to travel along the features of the needle actuator 60. This interaction results in displacement of the needle 16.

In a preferred embodiment, two sets of the detents 62 are provided, namely a spring set of detents 62a and a release set of detents 62b. The release detents 62b are located at or near the free end 54 of the needle driver 18. The spring detents 62a are located at a mid-location of the needle driver 18 between the fixed end 52 and the free end 54. It is preferred that the spring detents 62a and the release detents 62b be shaped and configured so as to provide a collective acting force that is evenly applied to the needle driver 18. Generation of moment about longitudinal axis 64 is undesired.

Figure 12:
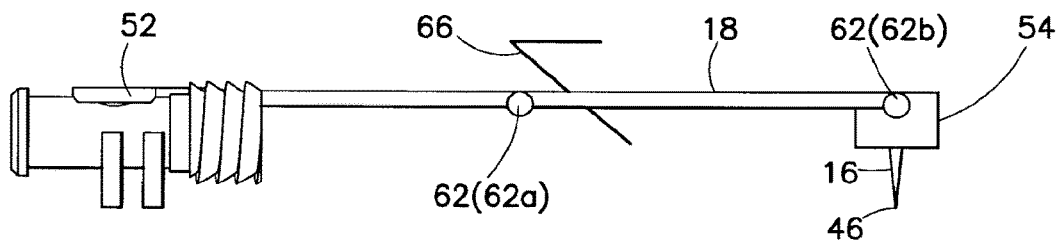
Figure 13:
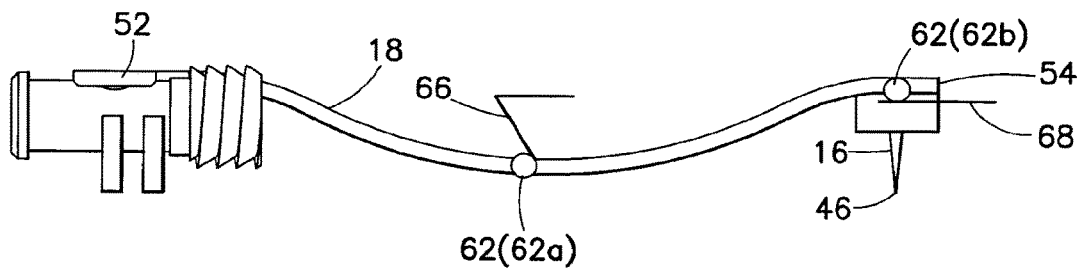
Figure 14:
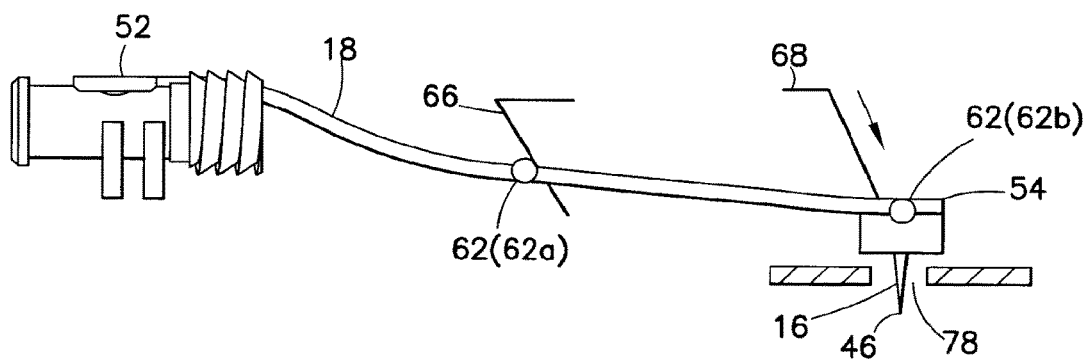
Figure 19:
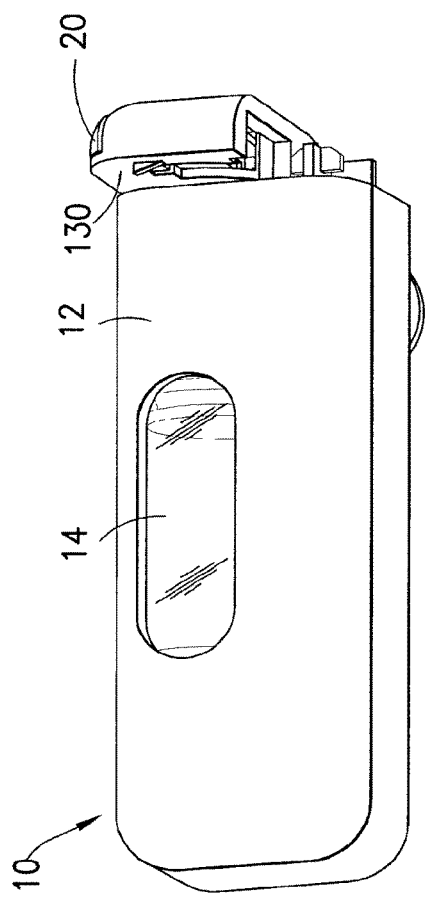

As shown in FIGS. 4 and 12, and discussed above, the needle driver 18 is preferably initially in a generally flat state prior to use. With actuation of the actuator 20, the needle actuator 60 is caused to be displaced relative to the needle driver 18 such that ramped surfaces 66 cause downward deflection of the spring detents 62a, as shown in FIG. 13. In this state, the release detents 62b are in engagement with stop surfaces 68. Due to the interengagement between the release detents 62b and the stop surfaces 68, deflection of the free end 54 is restrained. With sufficient movement of the needle actuator 60 relative to the needle driver 18, the release detents 62b are caused to come clear of the stop surfaces 68. The displacement of the spring detents 62a generates a spring force in the needle driver 18 which causes the free end 54 to be urged to return to its natural, flat state with the free end 54 being displaced downwardly (FIG. 14). This successive set of actions results in the needle 16 being displaced from the first state, shown in FIG. 12, to the second state, shown in FIG. 14. As discussed above, in the first state, the needle 16, particularly the distal end 46, is within the enclosed volume 24, while in the second state, the distal end 46 is exposed externally of the shell 22. The displacement of the needle 16 is utilized to cause the needle 16 to penetrate the skin of a patient for injection.

Once displaced, the needle driver 18 seeks to regain its initial flat configuration through inherent memory of its constituent material. As shown in FIG. 14, interengagement between the ramped surfaces 66 and the spring detents 62a maintains the needle 16 in the second state, penetrated in a patient.

As will be appreciated by those skilled in the art, other arrangements for causing displacement of the needle 16 may be utilized. For example, a releasable spring arrangement may be utilized, whereby the needle driver 18 is retained in the first state against spring force, with release of a retaining arrangement permitting the spring force to displace the needle driver 18 to the second state. Spring force may be supplied by various springs, such as compression springs, coil springs, elastomeric members, gas compression springs, and so forth.

Movement of the needle actuator 60 relative to the needle driver 18 may be provided by various configurations. Preferably, a needle actuator spring 70 is provided to act against the needle actuator 60 to cause displacement thereof.

Figure 5:
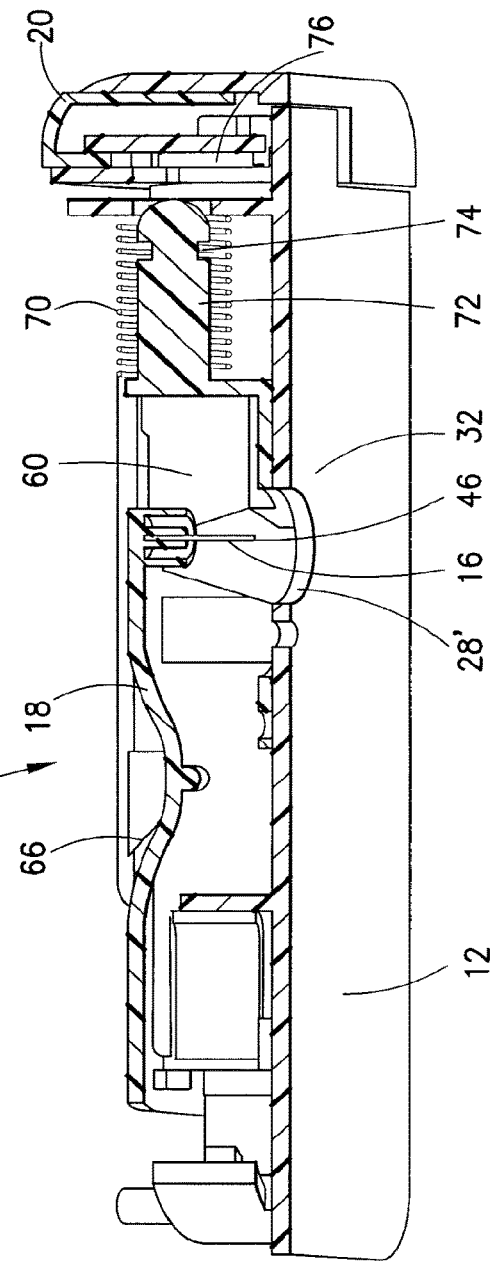

Various retaining arrangements may be provided for retaining the needle actuator 60 in a first state against force of the needle actuator spring 70, prior to use, as shown in FIG. 4. Preferably, the retaining arrangement is caused to be released with actuation of the actuator 20. By way of non-limiting example, and with reference to FIGS. 4-6, the retaining arrangement may include a boss 72 which extends from the needle actuator 60 to be engaged by the actuator 20. A locking channel 74 is defined in the boss 72 in which is seated a locking flange 76 in an initial, pre-use state. With displacement of the actuator 20 upon actuation, the locking flange 76 is caused to come out of engagement with the locking channel 74, as shown in FIG. 5. The locking flange 76 may be defined by a portion of the actuator 20. The needle actuator 60 is then caused to be displaced under force of the needle actuator spring 70.

Figure 44:
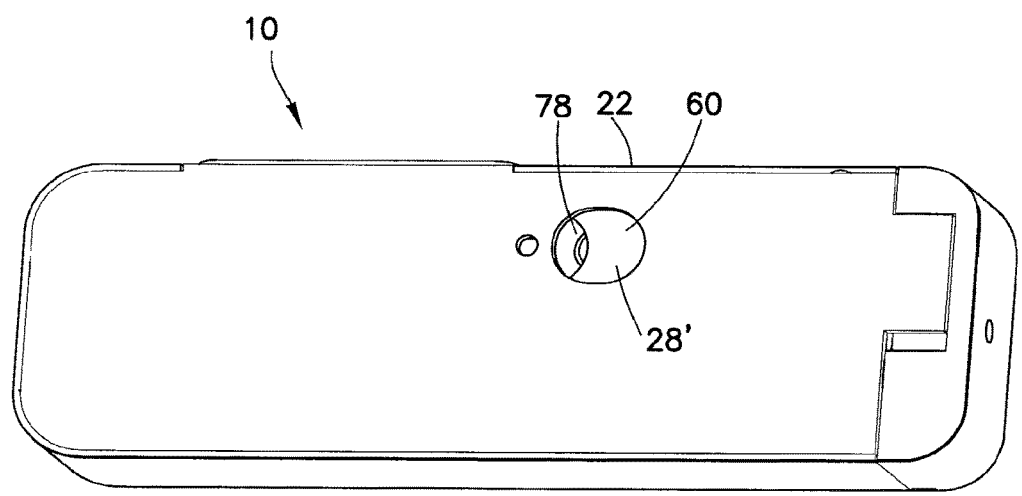
FIG. 44 is a rear perspective view showing a drug delivery device during use formed in accordance with the subject invention; and, FIGS. 45-47 show a safety pen and needle shield useable with the subject invention.

The travel of the needle actuator 60 may be limited with interengagement of a stop or similar member. A clearance opening 78 (FIG. 2) is formed in the needle actuator 60 through which the needle 16 passes upon displacement. The clearance opening 78 is in at least partial registration with the needle access opening 28' during displacement of the needle 16 to permit the needle 16 to achieve injection into a patient (FIG. 44). The needle access opening 28' is sized and configured to not interfere with the needle 16 during injection.

The clearance opening 78 may be configured to limit displacement of the needle driver 18 during actuation. In particular, the clearance opening 78 may be configured to permit passage therethrough of the needle 16 but not the needle driver 18. As such, interengagement between the needle driver 18 and portions of the needle actuator 60 adjacent to the clearance opening 78 acts as a limit on displacement of the needle driver 18. This defines the second state of the needle driver 18 and may define the depth of injection of the needle 16. Alternatively, the clearance opening 78 may be configured to not interferingly engage with the needle driver 18. In this manner, the patient's skin acts as a stop for the needle driver 18.

Figure 20:
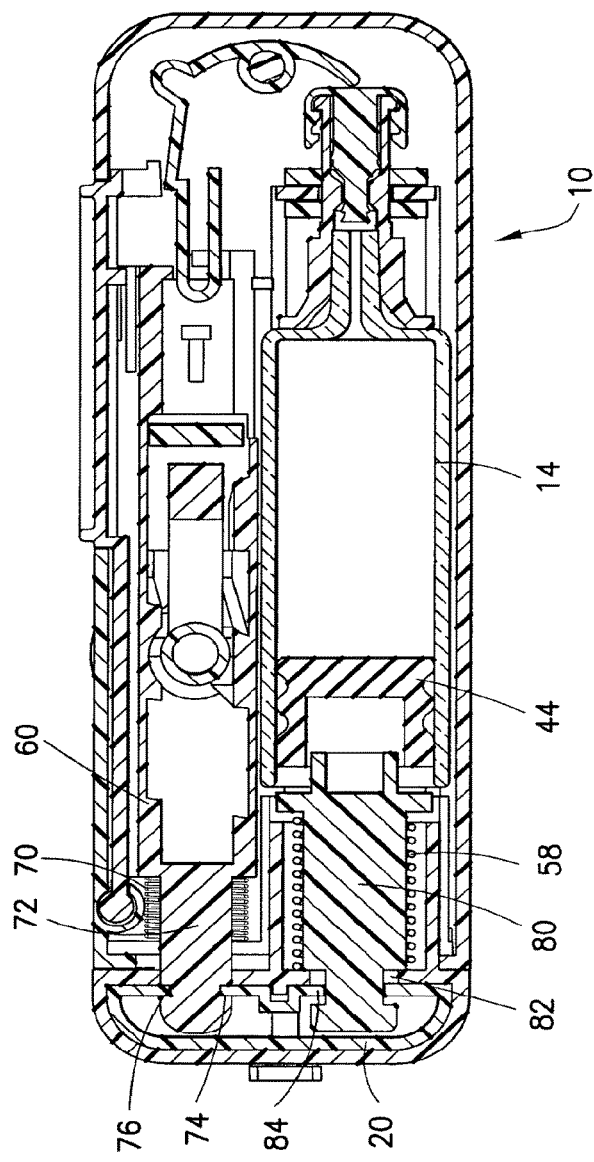
FIGS. 20 and 21 show an actuator arrangement useable with the subject invention.
Figure 21:
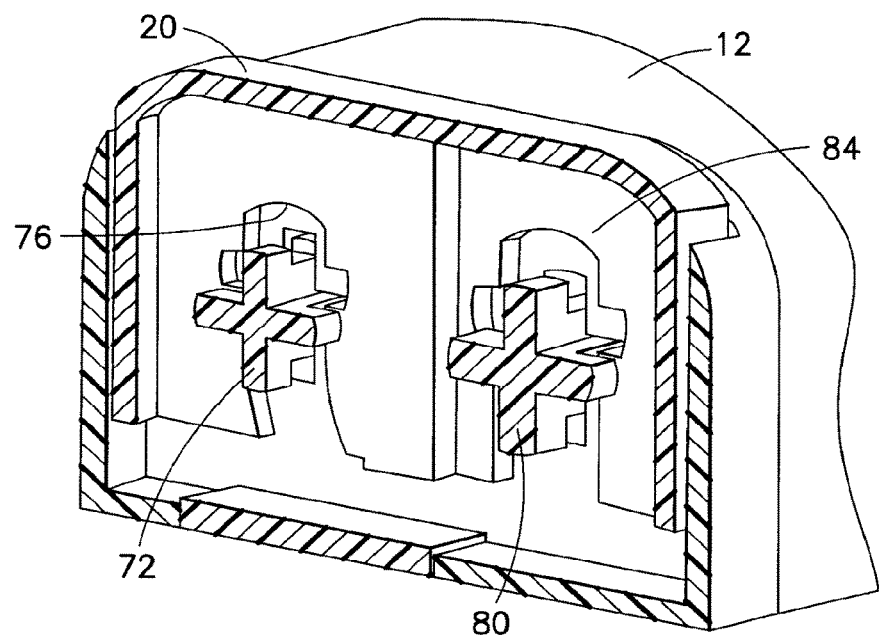

With respect to movement of the stopper 44, a retaining arrangement may be provided to restrain movement of the stopper 44 against force of the spring 58 in an initial, pre-use state. By way of non-limiting example, and with reference to FIGS. 20 and 21, a plunger 80 may be provided which is in engagement with the stopper 44 and formed to extend to be engageable by the actuator 20. A plunger locking channel 82 may be formed in the plunger 80, and a plunger locking flange 84 may be provided formed to seat in the plunger locking channel 82 in an initial, pre-use state. With displacement of the actuator 20, upon actuation, the plunger locking flange 84 is displaced so as to disengage from the plunger locking channel 82, thereby permitting displacement of the stopper 44 under force of movement of the spring 58. The plunger locking flange 84 may be defined by a portion of the actuator 20. As will be appreciated by those skilled in the art, a single actuation of the actuator 20 may result in release of both the stopper 44 and the needle actuator 60. For example, with reference to FIG. 21, the actuator 20 may define both the locking flange 76 and the plunger locking flange 84 such that displacement of the actuator 20 results in displacement of the locking flange 26 and the plunger locking flange 84 with simultaneous release of both the stopper 44 and the needle actuator 60.

With the drug delivery device 10 intended for use against a patient's skin, it is preferred that venting of the reservoir 14 or priming of the needle 16 not be required to administer medicament from the reservoir 14.

With the needle 16 being inserted into a patient, and the stopper 44 being caused to move, medicament may be displaced from the reservoir 14 through the flow channel 50 and administered to a patient via the needle 16, if there is direct communication between the lumen 42 of the needle 16 and the reservoir 14. As indicated above, it is preferred that a breachable seal arrangement or adjustable valve be utilized to provide indirect communication, with communication being achievable with breach of the seal arrangement and/or adjustment of the valve.

Figure 22:
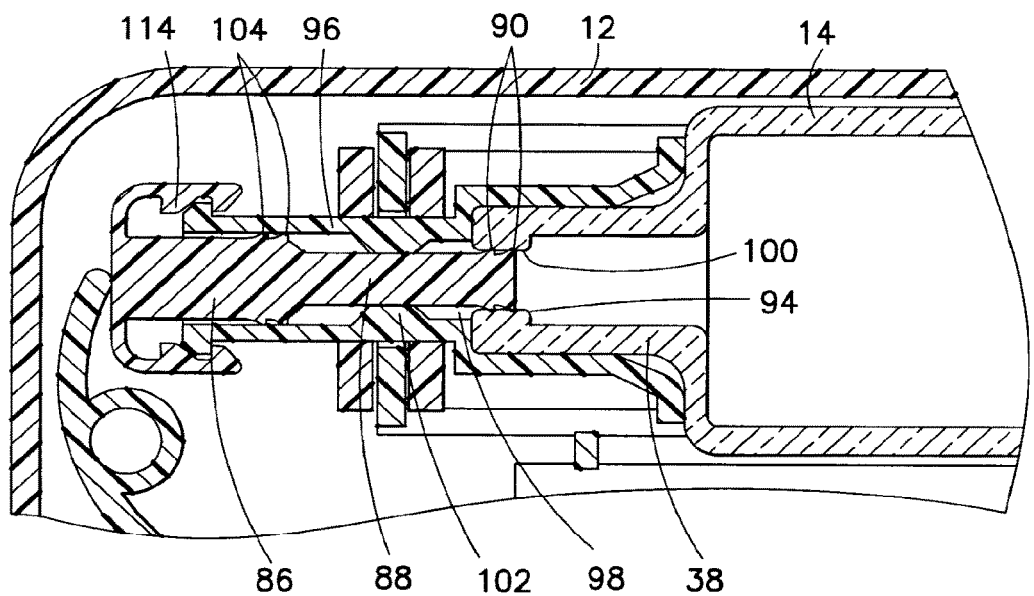
FIGS. 22-23 show different sealing arrangements useable with the subject invention.

In a preferred embodiment, an adjustable valve 86 may be utilized. With reference to FIG. 22, the valve 86 includes a valve stem 88 having one or more seal members 90. In one variation, as shown in FIG. 22, the seal members 90 may be configured to seal against a portion of the reservoir 14 in an initial state. In this manner, medicament contained within the reservoir 14 may be contained, during transportation and storage, within the reservoir 14. It is preferred that the reservoir 14 have a reduced diameter neck portion 92 at the first end 38 which defines exit opening 94. It is preferred that the valve 86 seal the reservoir 14 so as to contain the medicament wholly therewithin. In this manner, stability of the medicament in the reservoir 14, particularly during storage, may be better maintained. As indicated above, it is preferred that the reservoir 14 be formed of glass.

Figure 23:
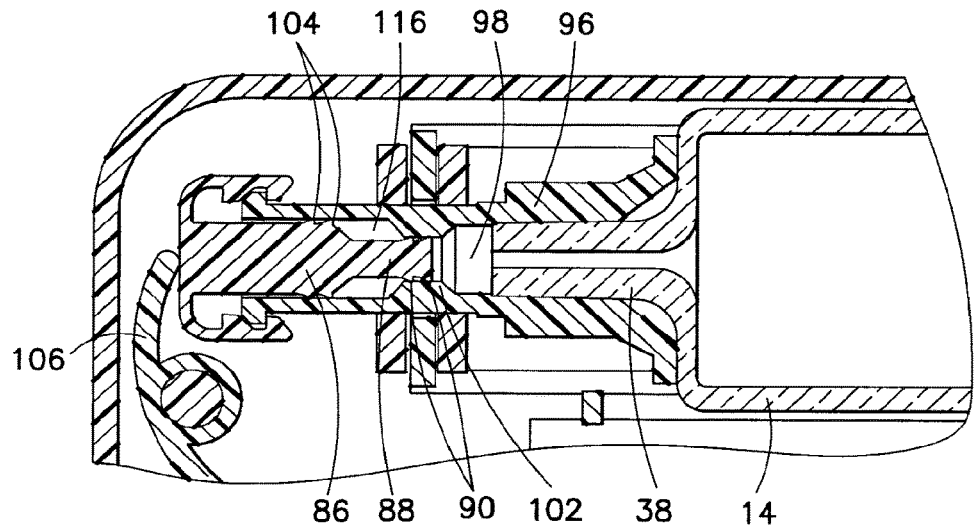

In a preferred arrangement, as shown in FIG. 23, an adaptor 96 may be provided in which the first end 38 of the reservoir 14 is seated. The first end 38 of the reservoir 14 may be formed in the same manner as a standard syringe tip, e.g., a Luer tip. A flow space 98 is provided in the adaptor 96 adjacent to, and in communication with, the reservoir 14. The seal members 90 are configured in this arrangement so as to seal the flow space 98 so as to prevent flow therefrom. With this arrangement, however, medicament may be in contact with portions of the adaptor 96, particularly portions of the adaptor 96 about the flow space 98 prior to use (e.g., during shipping and storage). The adaptor 96 may be formed of plastic or other polymeric material. Choice of materials for the valve 86 and the adaptor 96 should be considered in view of the medicament being stored in the reservoir 14.

To achieve flow from the reservoir 14, the valve 86 is made adjustable so as to adjust from a sealed, pre-use state, to an open, in-use state use. With reference to FIG. 22, in the alternative embodiment, the neck portion 92 preferably includes an inwardly extending lip 100 defined about the exit opening 94. In the initial state, as shown in FIG. 22, the seal members 90 seal against the lip 100 so as to seal the flow space 98 from the reservoir 14. To achieve the open state, the valve 86 is displaced such that the valve stem 88 shifts into the reservoir 14 with the seal members 90 coming out of sealing engagement with the lip 100. As such, a flow path is thus defined about the valve stem 88 and through the exit opening 94. The flow channel 50 may, thus, come into communication with the flow space 98. With the valve 86 being in the open state, and with the stopper 44 being caused to move, medicament is urged from the reservoir 14 through the exit opening 94, into the flow space 98, and into the flow channel 50 for administration to a patient. To provide sealing of the flow space 98, the adaptor 96 may be provided with a raised sealing ring 102 which comes into close contact with the valve stem 88. In addition, or alternatively, secondary seal members 104 may be provided on the valve 86 formed to define a seal with portions of the adaptor 96 to further restrict flow thereby.

In the preferred embodiment, shown in FIG. 23, the valve 86 may be adapted to form a seal in similar manner, here having the seal members 90 engage against and form a seal with the sealing ring 102 of the adaptor 96. Adjustment of the valve 86 towards the reservoir 14 causes disengagement of the seal members 90 from the sealing ring 102 to permit flow thereby. The flow channel 50 may be in communication with a secondary flow space 116, and the sealing ring 102 may be positioned between the secondary flow space 116 and the flow space 98. The secondary seal members 104 are provided to seal the secondary flow space 116 and prevent inadvertent flow therefrom.

Figure 2:
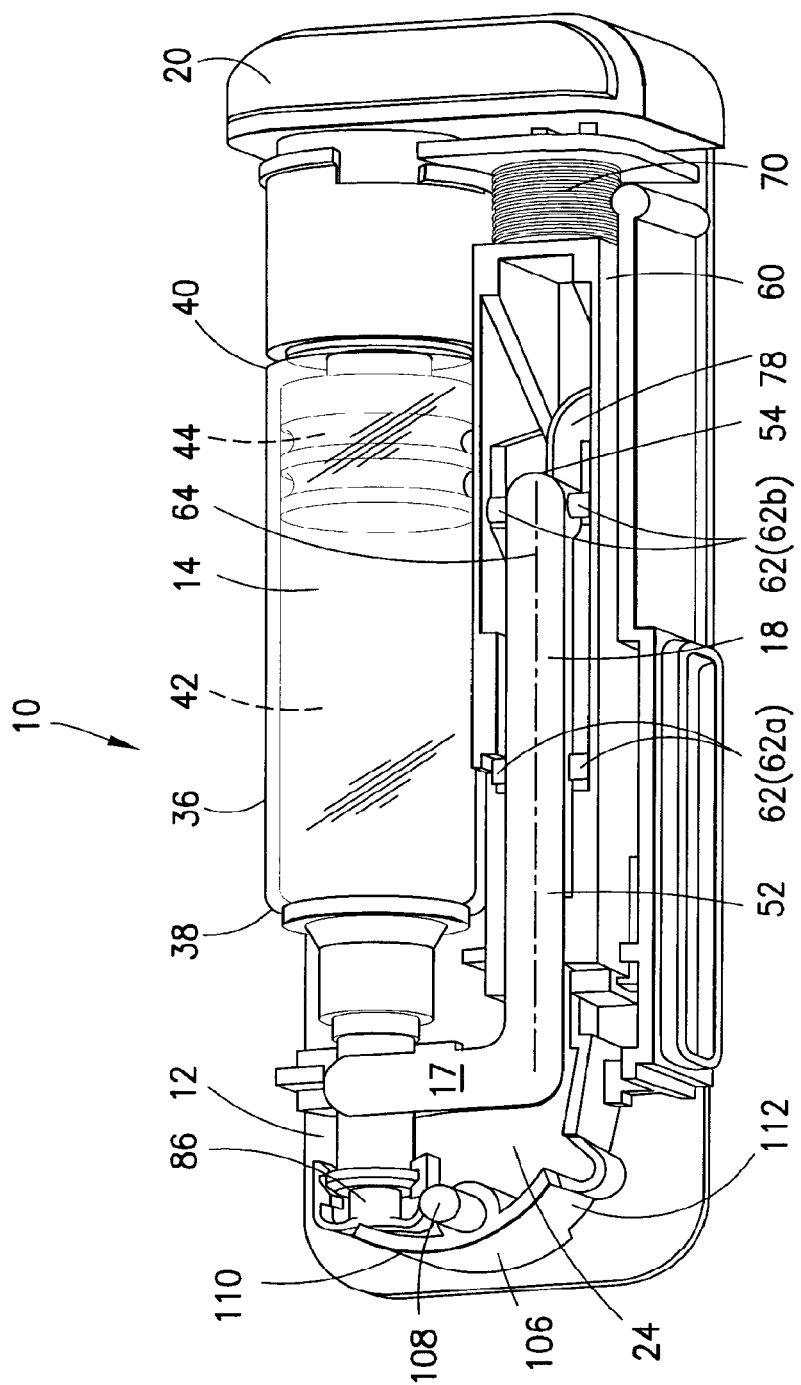
FIG. 2 is a perspective view of a drug delivery device formed in accordance with the subject invention with internal components being shown.

Adjustment of the valve 86 may be achieved in various manners. In a preferred embodiment, a pivoting valve rocker 106 may be utilized. As shown in FIGS. 2 and 8, the valve rocker 106 is mounted to a pivot pin 108 so as to be pivotable thereabout. A first arm 110 of the valve rocker 106 extends from the pivot pin 108 to be in engagement with the valve 86. A second arm 112 of the valve rocker 106 extends in an opposing direction from the pivot pin 108 so as to be in engagement with the needle actuator 60. As shown in FIG. 9, the valve rocker 106 is configured to be engaged by the needle actuator 60 upon sufficient movement relative to the needle driver 18. With sufficient movement of the needle actuator 60, the second arm 112 is caused to be displaced, resulting in pivoting movement of the valve rocker 106 and corresponding movement of the first arm 110 against the valve 86. Movement against the valve 86 results in adjustment thereof from the sealed state to the open state. More particularly, movement of the valve 86 results in shifting of the valve stem 88 into or towards the reservoir 14.

As shown in FIG. 22, the valve 86 may include a locking ring or tooth 114 for releasably retaining the valve 86 in the sealed state. The locking ring 114 is formed to resiliently release from the adaptor 96 under sufficient force of movement from the valve rocker 106. The locking ring 114 acts to prevent inadvertent adjustment of the valve 86 prior to use.

As will be appreciated by those skilled in the art, the reservoir 14 may be of various configurations. Preferably, a syringe barrel may be used to define the reservoir 14, particularly where the neck portion 92 is utilized. It is further preferred to use the sealing arrangement of FIG. 23 where a standard syringe may be utilized without modification. The reservoir 14 may be barrel-shaped with one end being selectively sealed by the valve 86. Alternatively, as shown in FIGS. 8-10 and 24-26, a secondary stopper 118 or a septum 120 may be utilized to seal the first end 38 of the reservoir 14. Here, the reservoir 14 may be in the form of a drug cartridge with the septum 120 sealing the exit opening 94 being defined in the neck portion 92 (FIG. 25). The septum 120 may be formed of any elastomeric material as is known in the art which permits piercing of therethrough, as described below. Alternatively, the reservoir 14 may include the secondary stopper 118 being located at or near the first end 38, spaced from the stopper 44 (FIG. 8). The secondary stopper 118 may be disposed in the lumen 48 so as to form a seal against the reservoir 14, as is known in the art.

Figure 24:
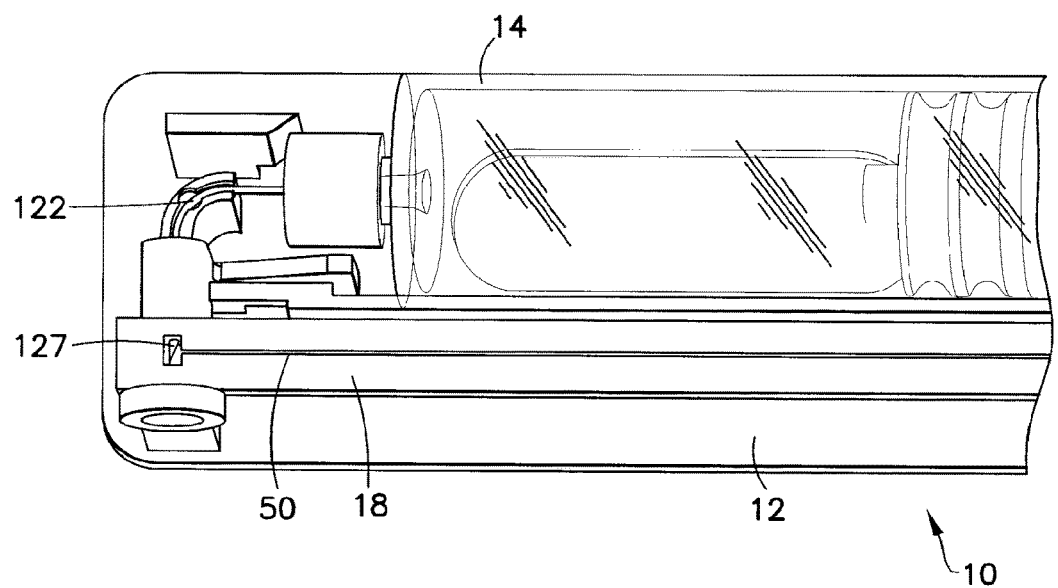
FIGS. 24-26 show a sealing arrangement with a secondary needle useable with the subject invention.
Figure 25:
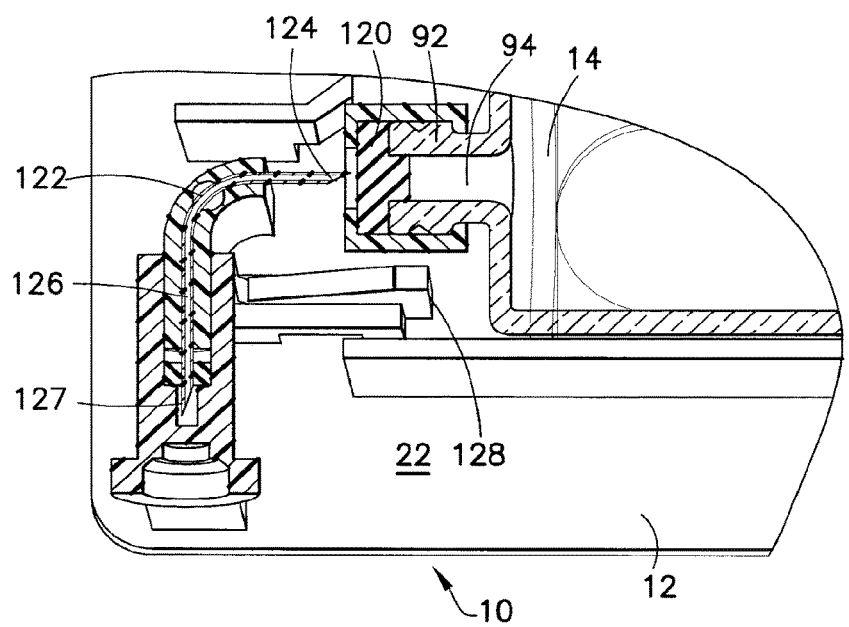
Figure 26:
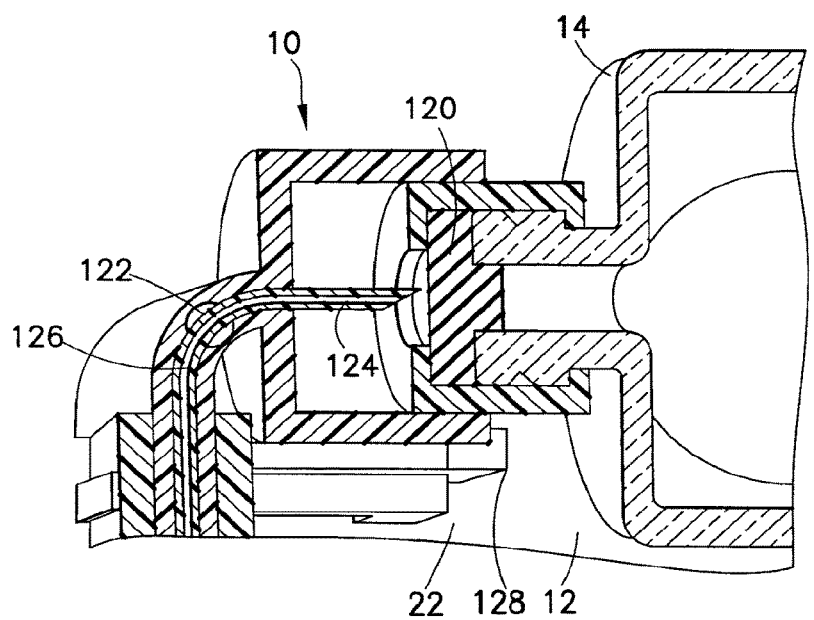
Figure 33:
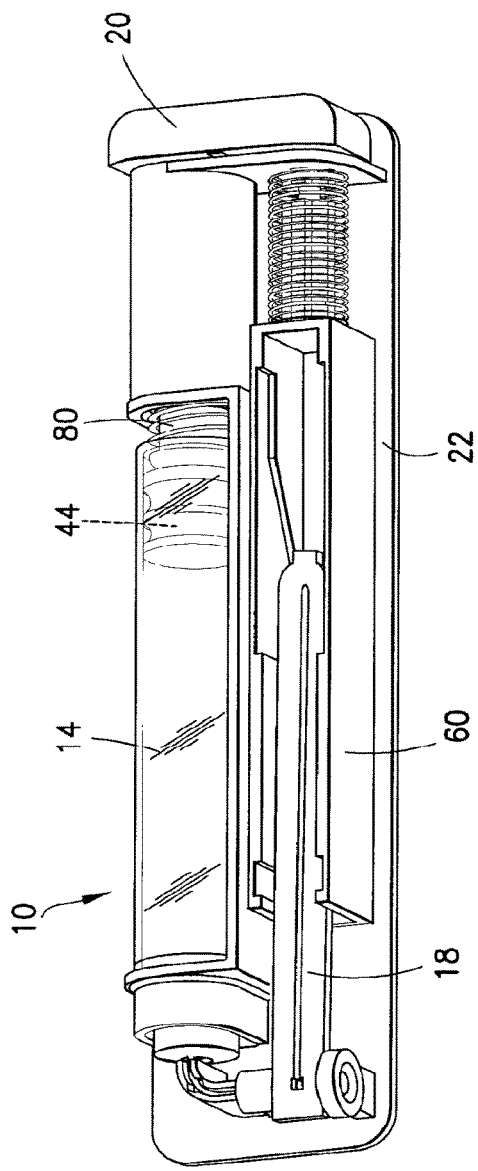
Figure 34:
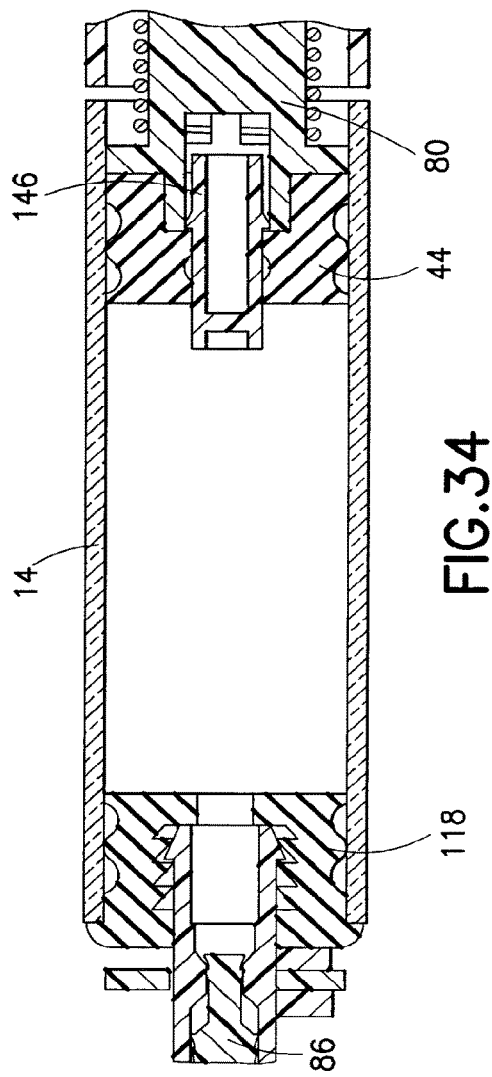
FIGS. 34-36 and 40 show an end-of-dose indicator useable with the subject invention.
Figure 35:
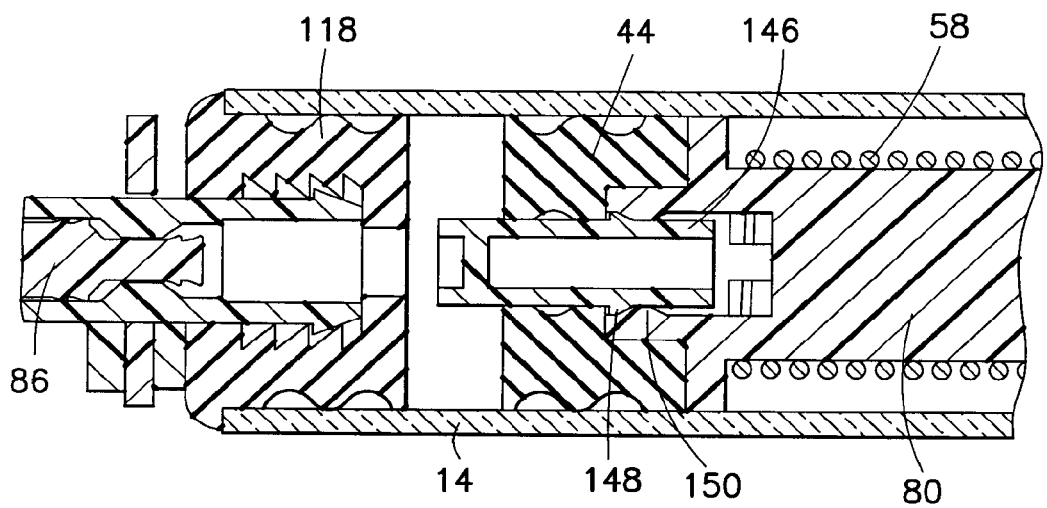

With the use of the secondary stopper 118 or the septum 120, access may be provided to the contents of the reservoir 14 through the use of a secondary needle 122 (FIGS. 24-26). The secondary needle 122 includes a first end 124 initially spaced from or partially embedded into the secondary stopper 118 or the septum 120. With relative movement between the secondary needle 122 and the reservoir 14, the first end 124 of the secondary needle 122 is caused to pierce through the secondary stopper 118 or the septum 120 so as to obtain access to the contents within the reservoir 14. Any mode of obtaining relative motion may be utilized. In a preferred arrangement, with the reservoir 14 being sealed by the secondary stopper 118 or the septum 120, the reservoir 14 may be caused to move under force of action of the spring 58 prior to the first end 124 of the secondary needle 122 piercing through the secondary stopper 118 or the septum 120. In a fully sealed state, and with the medicament being a liquid or a slurry, the medicament is generally incompressible with force being transmitted therethrough to allow for movement of the entire reservoir 14. With the secondary needle 122 accessing the contents of the reservoir 14, the further force applied to the stopper 44 by the spring 58 results in the medicament being urged into lumen 126 of the secondary needle 122 for administration to a patient. The secondary needle 122 is formed with a second end 127 in communication with the flow channel 50.

To limit inadvertent movement of the reservoir 14, one or more locking fingers 128 may extend from the shell 22 or other surrounding components to interferingly engage the reservoir 14 in limiting movement thereof With sufficient force being applied to the reservoir 14, the one or more locking fingers 128 may be caused to deform or be displaced so as to permit movement of the reservoir 14. The secondary needle 122 may be fixed to the shell 22 in any known manner. In addition, the secondary needle 122 may be bent or otherwise configured so as to permit the lumen 126 to come into contact with the flow channel 50.

With the use of the secondary needle 122, the second end 127 may be formed to extend into the needle driver 18 with the lumen 126 in communication with the flow channel 50 (FIG. 24). With actuation of the needle driver 18, the needle driver 18 may rotate about the secondary needle 122 while maintaining communication therewith. If the secondary needle 122 is not utilized, the driver 18 may be provided with an extension 17 through which the flow channel 50 extends into communication with the reservoir 14 (directly or indirectly) (FIG. 2).

The drug delivery device 10 may be pre-assembled and stored with medicament in the reservoir 14 prior to shipping and storage. With reference to FIGS. 27 and 28, the drug delivery device 10 may be prepared with the reservoir 14 being in a partially assembled state within the shell 22 and filled in this state. Thus, as shown in FIGS. 27 and 28, the reservoir 14 may be filled through the second end 40 through one of the access openings 28. Once filled, the stopper 44 may be inserted into the lumen 48 of the reservoir 14 to seal the reservoir 14 and the drug delivery device 10 may be fully assembled. With reference to FIG. 15, the reservoir 14 may be pre-assembled and pre-filled with medicament and then mounted to the shell 22 with one of the access openings 28. To ease manufacturing, one or more components of the drug delivery device 10 may be formed as a module, such as, for example, the plunger 80 may be provided together with the spring 58 and the actuator 20. Module housing 130 may be provided to accommodate the components in an assembled state.

In an alternative arrangement, and with reference to FIGS. 29-33, the reservoir 14 may be maintained separately from the drug delivery device 10 prior to use. For example, the reservoir 14 may be in the form of a drug cartridge. As shown in FIG. 29, the window 26 may be shaped and configured so as to permit the reservoir 14 to be passed therethrough into position within the shell 22. This motion is similar to the insertion of a battery into an appliance. One or more snap retaining members 132 may be provided to engage the reservoir 14 to provide retention therefor in a desired position. In the desired position, the stopper 44 is positioned to align with the plunger 80 and the exit opening 94 is positioned to align with the secondary needle 122 so as to permit piercing thereof. The reservoir 14 may be in the form of a constant-diameter barrel having the stopper 44 and the septum 120 with the reservoir 14 being insertable through the window 26 in the same manner as described above with the reservoir 14 being in the form of a drug cartridge.

Figure 37:
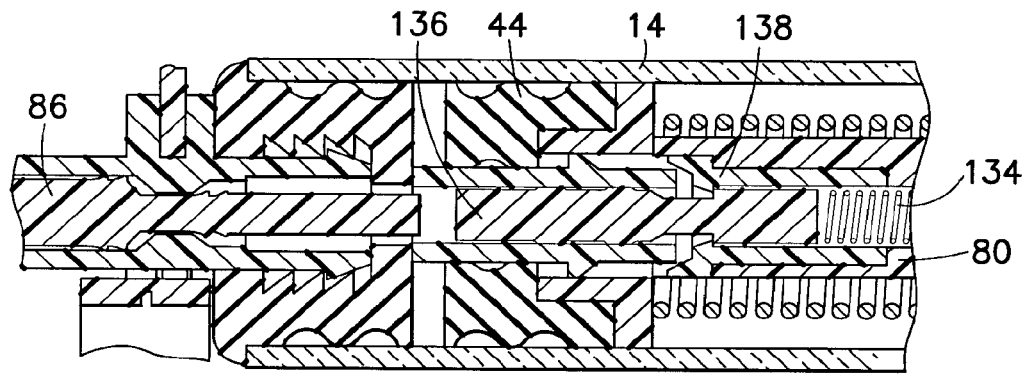
FIGS. 37-39 show a mechanism for achieving needle retraction useable with the subject invention.
Figure 38:
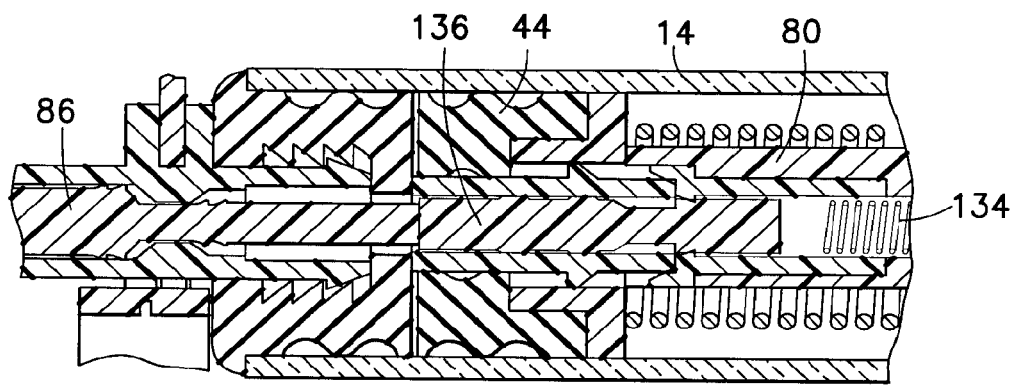
Figure 39:
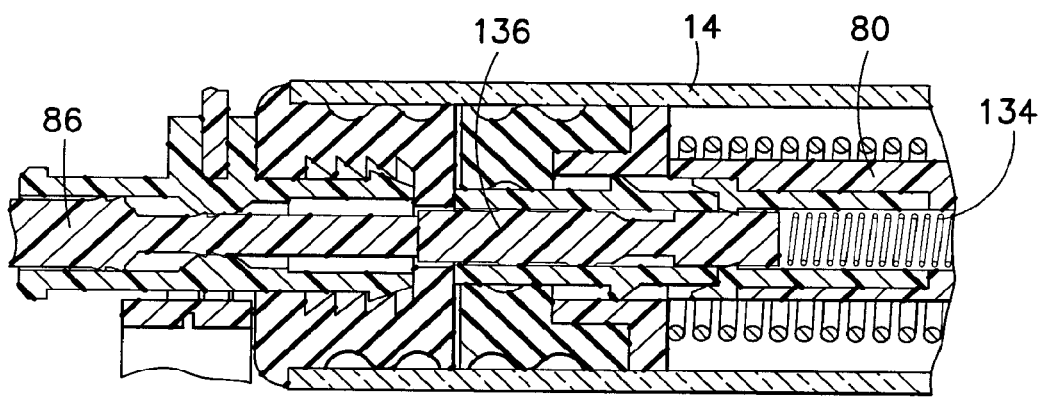

As will be appreciated by those skilled in the art, the drug delivery device 10 may include additional features beyond those described above. For example, it may be desired to provide for retraction of the needle 16 post-use. The needle 16 may be caused to retract in various manners. With reference to FIGS. 37-39, in one approach, the needle actuator 60 is caused to move in a reverse direction relative to the needle driver 18, this direction being opposite to the original direction of movement used to cause displacement of the needle 16. By way of non-limiting example, as shown in FIGS. 37-39, a drive spring 134 may be disposed within the plunger 80, which is disposed to act against secondary plunger 136. The secondary plunger 136 is held in an initial position due to interengagement with latch 138. With the stopper 44 reaching the end of its full travel, the latch 138 is caused to be released with the secondary plunger 136 being driven forwardly under force of the drive spring 134. The secondary plunger 136 is caused to engage against the valve 86, applying force thereto so as to shift the valve 86 to return towards its initial state. The valve 86, thus, acts against the valve rocker 106 with resulting reverse pivoting movement towards its original state. In response, the valve rocker 106 acts against the needle actuator 60 so as to urge the needle actuator 60 to its original state. With movement of the needle actuator 60 to its original state, displacement of the needle driver 18 is reversed and the needle 16 is caused to retract.

Figure 7:
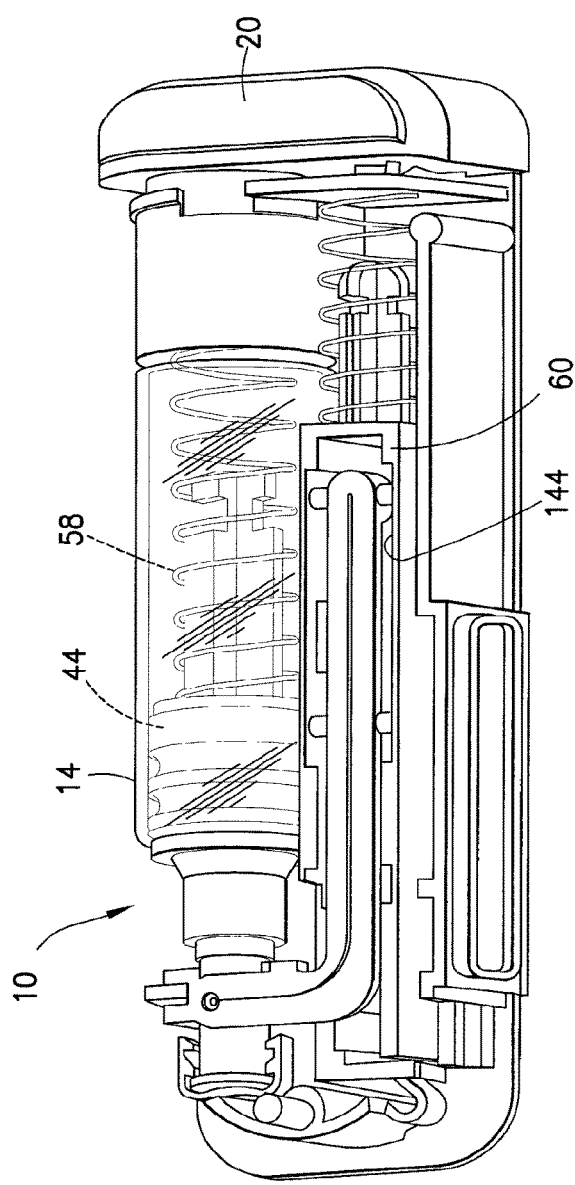
Figure 10:
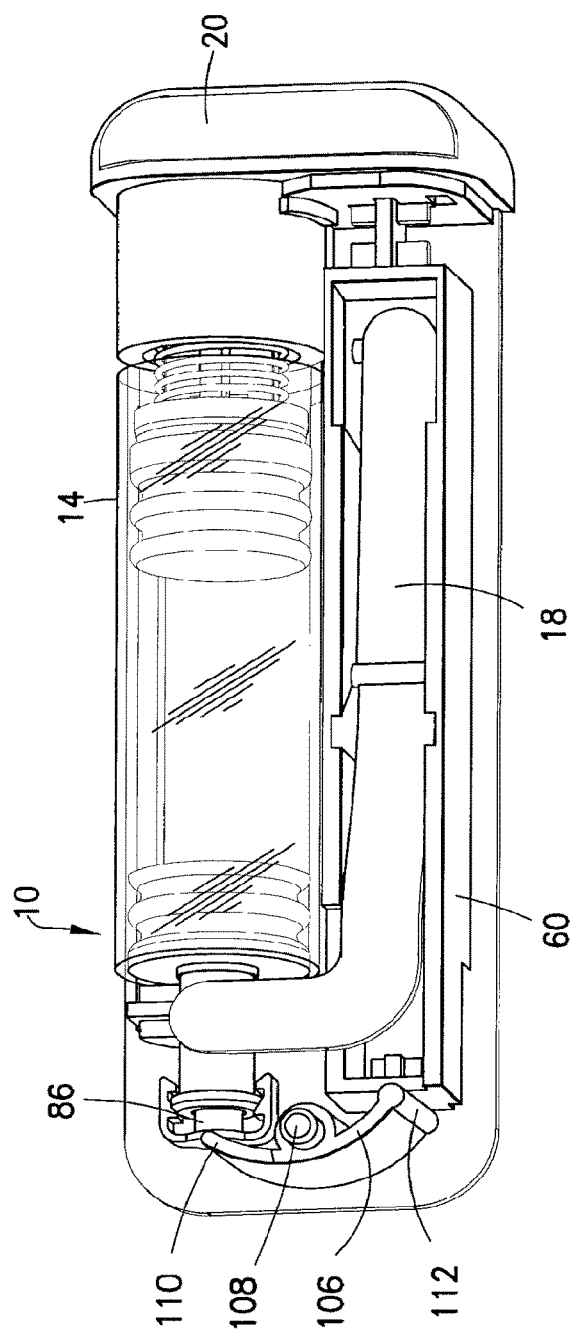
Figure 11:
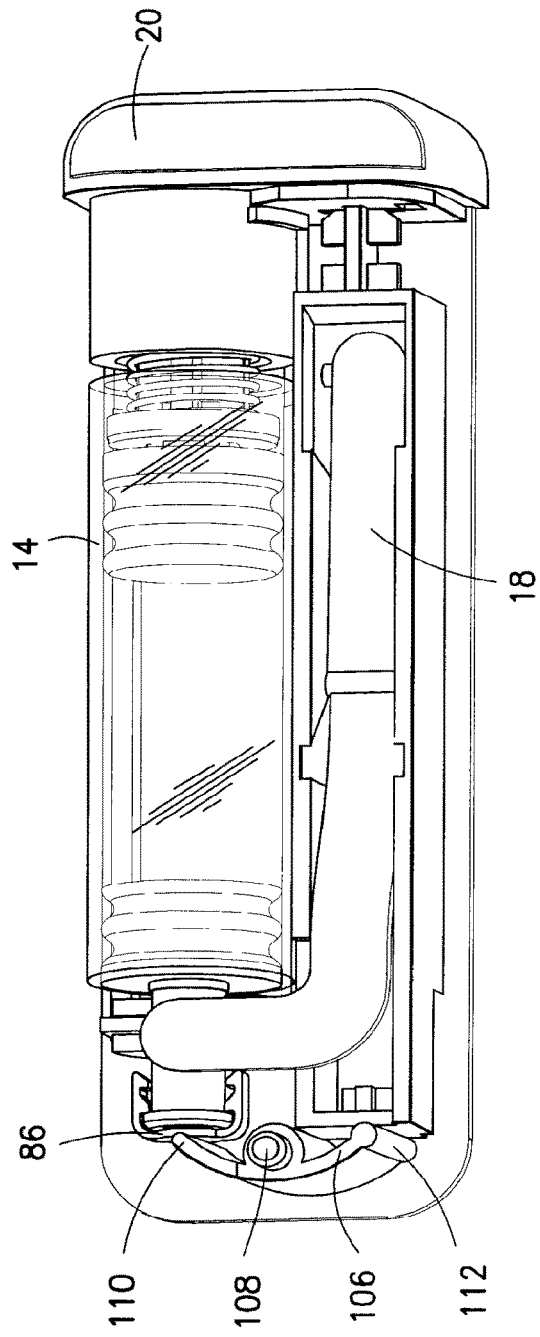
Figure 40:
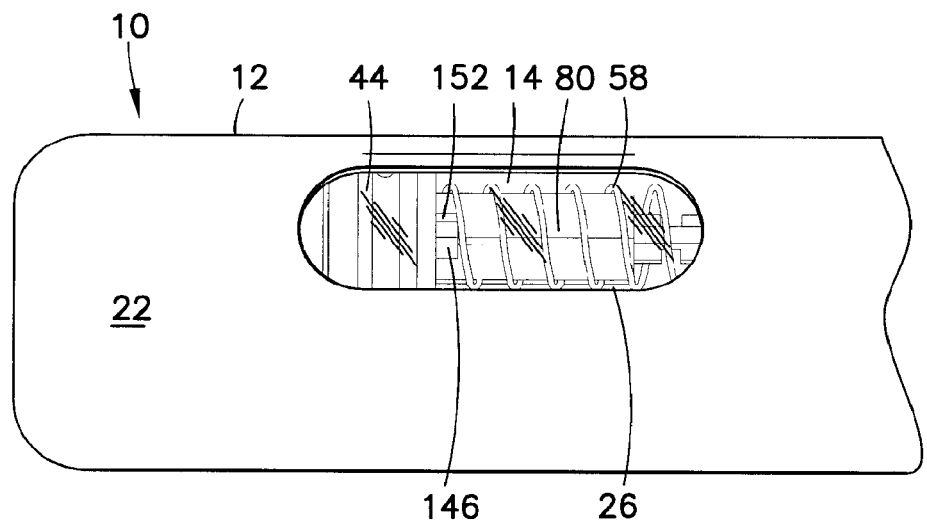
Figure 41:
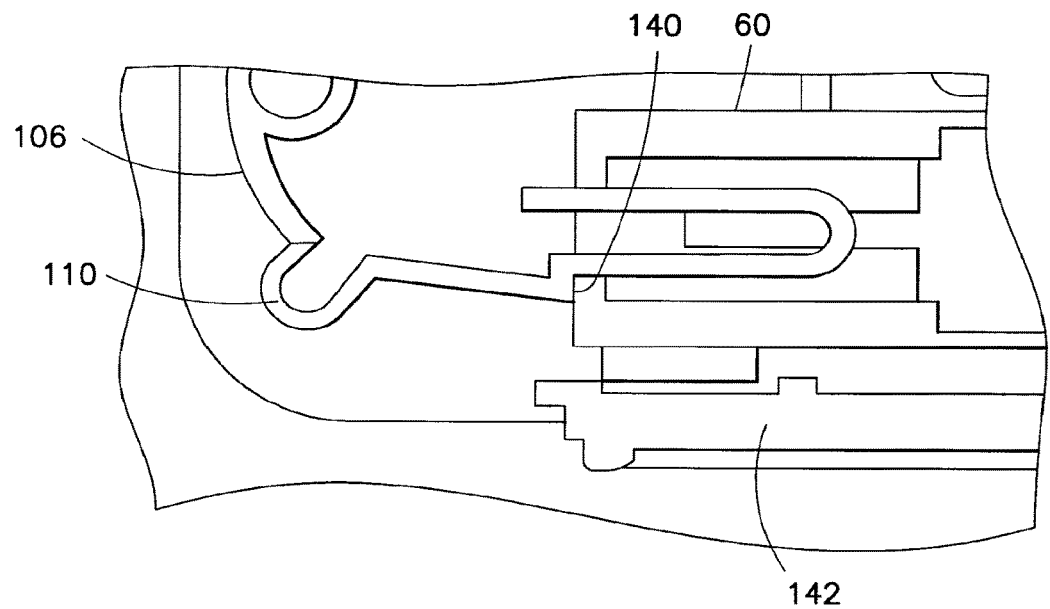
FIGS. 41-43 show a button-releaseable mechanism for needle retraction useable with the subject invention.
Figure 42:
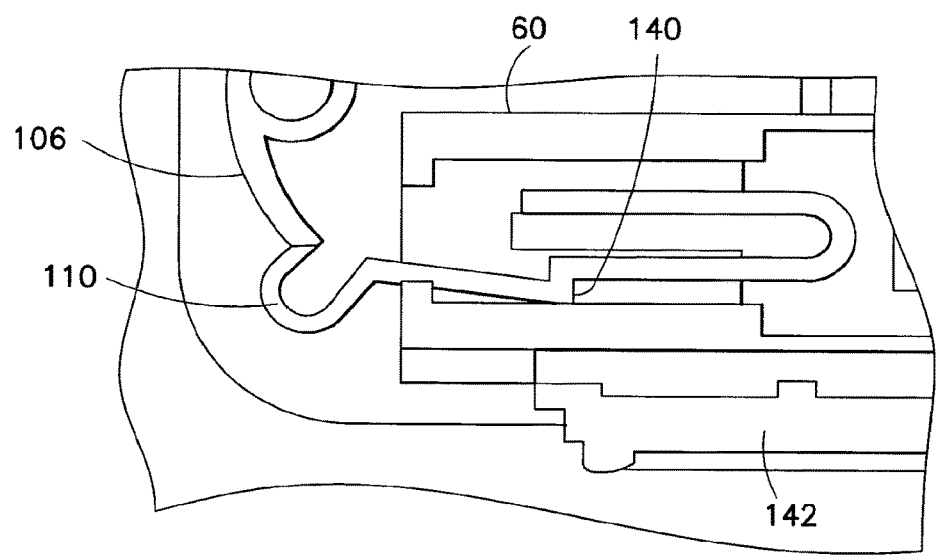
Figure 43:
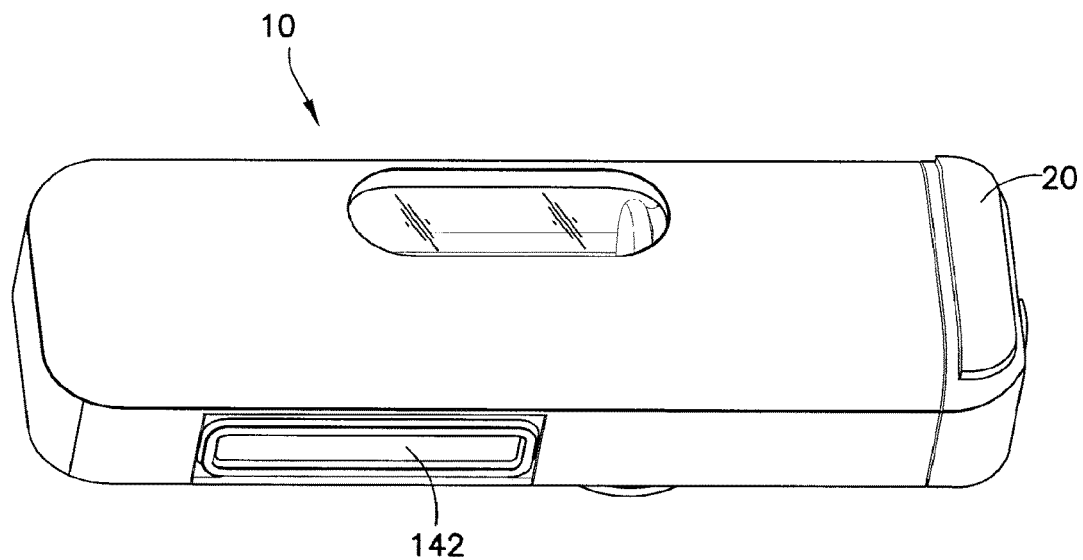

In a preferred embodiment, as shown in FIGS. 41-43, the first arm 110 of the valve rocker 106 may be bent or otherwise configured to define a stop 140, positioned to engage the needle actuator 60 upon a predetermined extent of movement relative to the needle driver 18. The stop 140 is positioned to allow sufficient movement of the needle actuator 60 to permit the needle 16 to be displaced for injection. A secondary actuator 142, which is preferably in the form of a linearly displaceable button, is positioned to press against the stop 140 to cause disengagement from the needle actuator 60. With disengagement, the needle actuator 60 is free to further travel under force of the needle actuator spring 70 (FIG. 42). Secondary ramp surfaces 144 are positioned to engage against the release detents 62$b$ so as to cause retraction of the needle 16 into the shell 22 (FIG. 7). Furthermore, as shown in FIG. 40, this movement of the needle actuator 60 causes the clearance opening 78 to come out of alignment with the needle access opening 28', thus further limiting access to the needle 16.

Figure 36:
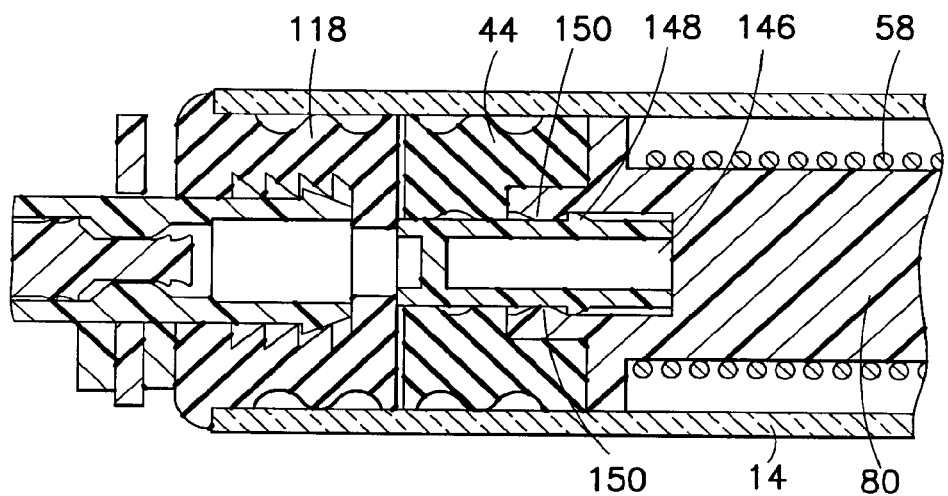

The drug delivery device 10 may be also provided with an end-of-dose indicator to provide a sensory indication that a dose has been completely administered. With reference to FIGS. 34-36 and 40, the plunger 80 may be provided with an indicator sleeve 146 that is formed to extend through the stopper 44 in an initial state. The indicator sleeve 146 includes a ridge 148. The plunger 80 is provided with outwardly displaceable engagement members 150 located to restrict movement of the indicator sleeve 146 away from the stopper 44. With the plunger 80 being moved by the spring 58 to urge medicament from the reservoir 14, the stopper 44 eventually comes to an end-of-travel with engagement against a portion of the reservoir 14 and/or against the secondary stopper 118. This position will coincide with the end of the dosing stroke. As shown in FIG. 36, the indicator sleeve 146 will be engaged by a portion of the reservoir 14 and/or the secondary stopper 118 prior to engagement by the stopper 44. Further force applied to the stopper 44 by the plunger 80 causes displacement of the engagement members 150 over the ridge 148. The plunger 80 is provided with one or more indicator windows 152. In the initial state, the indicator sleeve 146 is out of alignment with the indicator windows 152. Upon being displaced at the end of the dosing stroke, a portion of the indicator sleeve 146 comes into alignment with the one or more indicator windows 152 so as to be visually observable from outside the plunger 80 (FIG. 40). One or more of the windows 26 in the shell 22 may be aligned so as to permit observation of the indicator sleeve 146 through the indicator windows 152. Preferably, the indicator sleeve 146 is formed of a different color from the plunger 80 so as to be readily discernable. It is also noted that the surmounting of the ridge 148 by the engagement members 150 may also provide a tactile and/or audible indication of end-of-dose administration.

Figure 3:
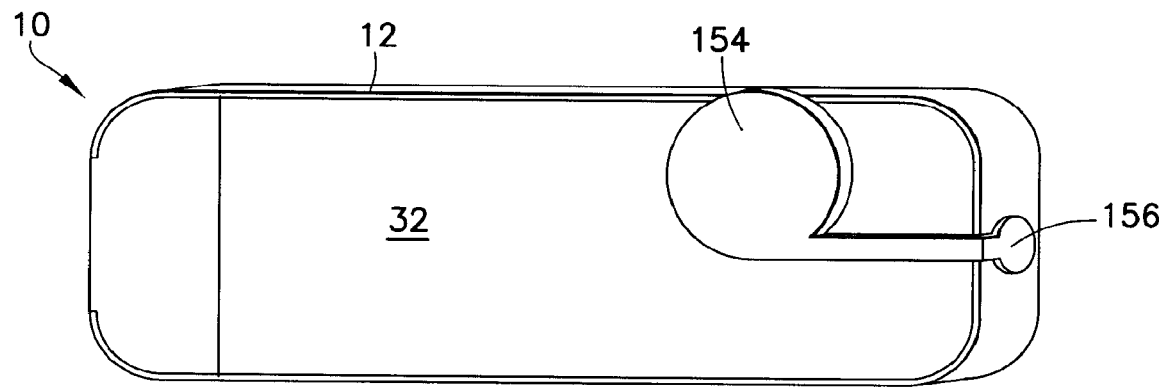
FIG. 3 is a rear perspective view of a drug delivery device formed in accordance with the subject invention.

With reference to FIG. 3, it is also noted that a needle shield 154 may be provided to cover the needle access opening 28' prior to use. The needle shield 154 may be secured, such as by friction fit into the needle access opening 28'. A finger tab 156 may be provided to extend from the needle shield 154, particularly beyond the perimeter of the shell 22 to ease removal of the needle shield 154.

Figure 45:
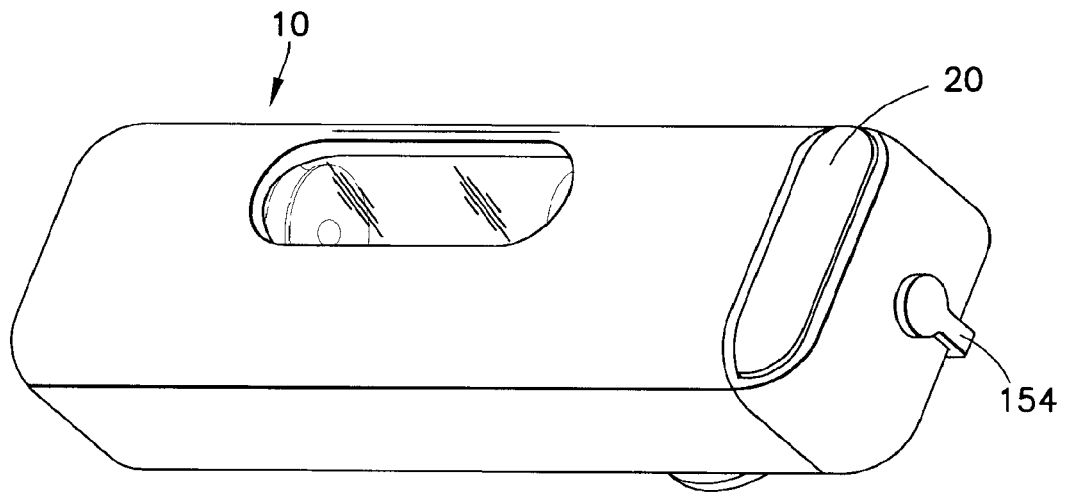
Figure 46:
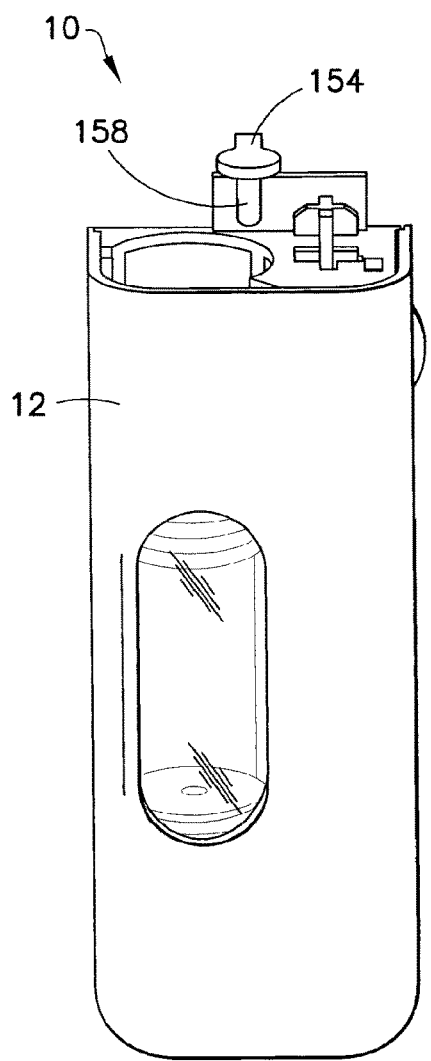
Figure 47:
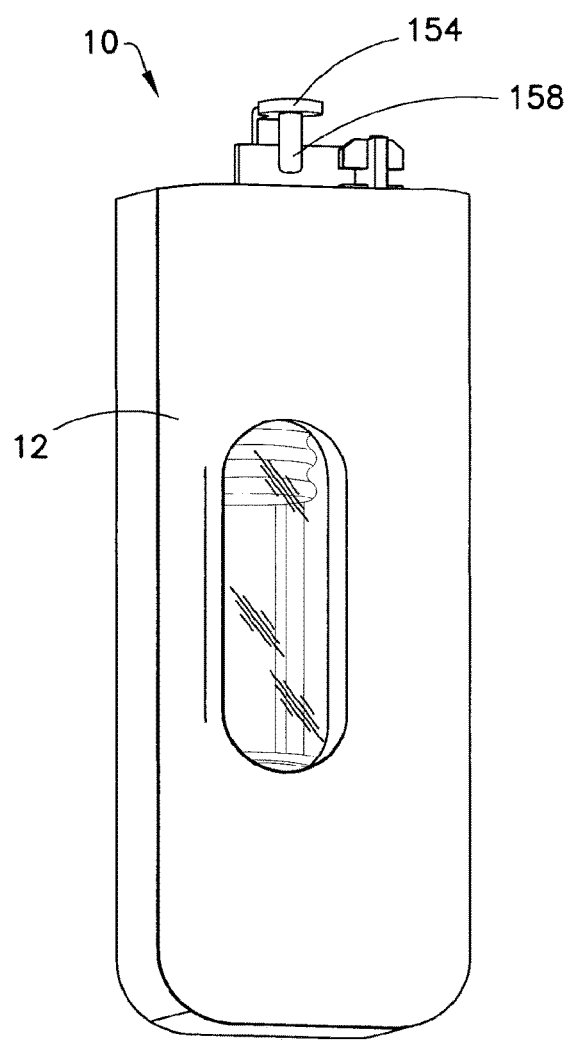

A safety pin 158 may also be provided and formed to coact with the actuator 20 so as to prevent inadvertent actuation thereof. With reference to FIGS. 45-47, the safety pin 158 may be formed to extend into the actuator 20 so as to prevent displacement thereof. The safety pin 158 is required to be removed so as to permit actuation of the actuator 56. The safety pin 158 may be formed unitarily with the needle shield 154 such that with single removal of the needle shield 154/the safety pin 158 assembly, the drug delivery device 10 may be readied for use.

What is claimed is:

1. A drug delivery device for injecting medicament, the drug delivery device comprising:
    a body;
    a reservoir movably disposed in the body for accommodating a medicament, the reservoir extending along a longitudinal axis;
    a needle, the needle having a distal end for insertion into a patient, and a lumen extending proximally from the distal end, the lumen being connectable with the reservoir, wherein, at least a portion of the lumen extends proximally from the distal end along a reference axis that is not parallel with the longitudinal axis;
    a first spring adapted to move the reservoir from a first reservoir position to a second reservoir position in the body to establish communication with the needle;
    a second spring;
    a needle driver adapted to displace the needle from a first state to a second state, the needle being disposed at an end of the needle driver; and
    a needle actuator displaced within the body relative to the driver by the second spring, wherein during its displacement, the needle actuator interacts with the needle driver to cause the needle displacement from the first state to the second state.

2. A drug delivery device as in claim 1, further comprising a device actuator;
    wherein activation of the device actuator causes:
    the first spring to move the reservoir from the first position and toward the second position; and
    the second spring to displace the needle actuator to cause the needle driver to displace the needle from the first state and toward the second state, wherein, the needle moves relative to, and separately from, the reservoir with the needle being displaced from the first state and toward the second state.

3. A drug delivery device as in claim 1, further comprising a flow channel in communication with the lumen of the needle, the flow channel being selectively communicable with the reservoir, wherein in an initial state, the flow channel not being in communication with the reservoir.

4. A drug delivery device as in claim 1 further comprising an adhesive for removably adherently securing the device to a patient.

5. A drug delivery device as in claim 1, wherein the needle driver includes a cantilevered arm, deformation of the cantilevered arm causing displacement of the needle from the first state and toward the second state.

6. A drug delivery device as in claim 1 further comprising an indicator for indicating that dosage delivery is complete.

7. A drug delivery device as in claim 1, wherein a window is formed in the body to permit viewing of at least a portion of the reservoir.

8. A drug delivery device as in claim 1 wherein, in the first state, the distal end of the needle is disposed within the body, and, wherein, in the second state, the distal end of the needle is exposed externally of the body.

9. A drug delivery device as in claim 1, wherein:
    the needle driver includes a first interacting feature;
    the needle actuator includes a second interacting feature; and
    during the needle actuator displacement, the first and second interacting features interact to displace the needle from the first state to the second state.

10. A drug delivery device as in claim 9, wherein the first interacting feature includes a detent; and
    the second interacting feature includes a ramp surface.

11. A drug delivery device as in claim 1, wherein:
    the needle driver includes a first interacting feature;
    the needle actuator includes a ramp; and
    during the needle actuator displacement, the ramp contacts the first interacting feature and a shape of the ramp and the interaction of the ramp and the first interacting feature displaces the needle from the first state to the second state.

* * * * *